United States Patent
Ninomiya

(10) Patent No.: US 11,061,470 B2
(45) Date of Patent: Jul. 13, 2021

(54) EYE TRACKING DEVICE AND EYE TRACKING METHOD

(71) Applicant: JVCKENWOOD Corporation, Yokohama (JP)

(72) Inventor: Masaru Ninomiya, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 0 days.

(21) Appl. No.: 16/578,501

(22) Filed: Sep. 23, 2019

(65) Prior Publication Data

US 2020/0019241 A1 Jan. 16, 2020

Related U.S. Application Data

(63) Continuation of application No. PCT/JP2018/011194, filed on Mar. 20, 2018.

(30) Foreign Application Priority Data

Aug. 2, 2017 (JP) .............................. JP2017-149684

(51) Int. Cl.
*G06F 3/01* (2006.01)
*G06T 7/70* (2017.01)
*H04N 5/235* (2006.01)

(52) U.S. Cl.
CPC ............... *G06F 3/013* (2013.01); *G06T 7/70* (2017.01); *H04N 5/2354* (2013.01); *G06T 2207/10012* (2013.01); *G06T 2207/30201* (2013.01)

(58) Field of Classification Search
None
See application file for complete search history.

(56) References Cited

U.S. PATENT DOCUMENTS 5,644,642 A * 7/1997 Kirschbaum .......... A61B 3/102
382/103
2015/0238087 A1 8/2015 Yamashita et al.
(Continued)

FOREIGN PATENT DOCUMENTS

EP 2604180 6/2013
EP 3011894 4/2016
(Continued)

OTHER PUBLICATIONS

International Search Report and Written Opinion for International Patent Application No. PCT/JP2018/011194 dated Jun. 12, 2018, 12 pages.
(Continued)

*Primary Examiner* — Stuart D Bennett
(74) *Attorney, Agent, or Firm* — Amin, Turocy & Watson, LLP

(57) ABSTRACT

An eye tracking device includes at least one light source configured to irradiate detection light for eye tracking to at least one eyeball of a subject; at least one imager configured to capture image of the at least one eyeball; a position detecting unit configured to detect a position of a pupil center of the at least one eyeball and a position of a corneal reflex center of the at least one eyeball from the captured image; a gaze determining unit configured to determine whether the subject is gazing at a target position based on the position of the pupil center and the position of the corneal reflex center; and a calibration unit configured to perform calibration for the eye tracking based on the captured image when the gaze determining unit determines that the target position is gazed at by the subject.

4 Claims, 15 Drawing Sheets

(56) References Cited

U.S. PATENT DOCUMENTS

2016/0113486 A1    4/2016  Ninomiya et al.
2017/0105619 A1    4/2017  Ebisawa
2017/0329400 A1*  11/2017  Noda .................... A61B 3/113

FOREIGN PATENT DOCUMENTS

| JP | 2016-085588  | 5/2016  |
| WO | 2014/073645  | 5/2014  |
| WO | 2015/190204  | 12/2015 |
| WO | 2016/098406  | 6/2016  |

OTHER PUBLICATIONS

Extended European Search Report for European Patent Application No. 18840864.5 dated May 14, 2020.
European Office Action for European Patent Application No. 18840864.5 dated Mar. 3, 2021.

\* cited by examiner

FIRST CALIBRATION PROCESSING

GAZE POINT DETECTION PROCESSING

EYE TRACKING DEVICE AND EYE TRACKING METHOD

CROSS-REFERENCE TO RELATED APPLICATIONS

This application is a continuation of PCT International Application No. PCT/JP2018/011194 filed in Japan on Mar. 20, 2018, which claims priority to and incorporates by references the entire contents of Japanese Patent Application No. 2017-149684 filed in Japan on Aug. 2, 2017.

FIELD

The present application relates to an eye tracking device and an eye tracking method.

BACKGROUND

An eye tracking device that detects a position at which an operator or a subject gazes on an observation surface, such as a monitor screen, have been proposed. On eye tracking, there is a case in which non-contact eye tracking without a device mounted on a face of the operator or the subject is applied. In this case, the eye tracking device irradiates detection light to an eyeball of the operator or the subject, calculates a pupil center and a corneal reflex position from an image of the eyeball to which the detection light is irradiated, and detects a position at which the operator or the subject gazes on an observation surface, such as the monitor screen. Moreover, for the eye tracking device, a method in which calibration is performed per operator or subject by having the operator or the subject gaze at a certain target position present on a monitor screen, to detect a line of sight of the subject or the operator more accurately has been proposed (Japanese Laid-open Patent Publication No. 2016-85588).

SUMMARY

However, because the calibration is performed assuming that a certain target position present on a monitor screen is gazed, accuracy of calibration can be deteriorated when the subject is not gazing at the target position.

An eye tracking device and an eye tracking method are disclosed.

According to the present application, there is provide an eye tracking device comprising: at least one light source configured to irradiate detection light for eye tracking to at least one eyeball of a subject; at least one imager configured to capture image of the at least one eyeball; a position detecting unit configured to detect a position of a pupil center of the at least one eyeball and a position of a corneal reflex center of the at least one eyeball from the image captured by the at least one imager; a gaze determining unit configured to determine that the subject is gazing at a target position when a distance between the position of the pupil center and the position of the corneal reflex center detected by the position detecting unit falls within a range of a predetermined distance threshold, and determines that the subject is not gazing at the target position when the distance between the position of the pupil center and the position of the corneal reflex center falls outside the range of the predetermined distance threshold; and a calibration unit configured to perform calibration for the eye tracking based on the image captured by the at least one imager when the gaze determining unit determines that the target position is gazed at by the subject.

According to the present application, there is provide an eye tracking method comprising: a detection light irradiating step of irradiating detection light for eye tracking to at least one eyeball of a subject; an imaging step of capturing image of the at least one eyeball; a position detecting step of detecting a position of a pupil center of the at least one eyeball and a position of a corneal reflex center of the at least one eyeball from the image captured at the imaging step; a gaze determining step of determining that the subject is gazing at a target position when a distance between the position of the pupil center and the position of the corneal reflex center detected at the position detecting step falls within a range of a predetermined distance threshold, and determines that the subject is not gazing at the target position when the distance between the position of the pupil center and the position of the corneal reflex center falls outside the range of the predetermined distance threshold; and a calibration step of performing calibration for the eye tracking based on the image captured at the imaging step when it is determined that that the target position is gazed at by the subject the gaze determining step.

The above and other objects, features, advantages and technical and industrial significance of this application will be better understood by reading the following detailed description of presently preferred embodiments of the application, when considered in connection with the accompanying drawings.

DETAILED DESCRIPTION OF THE PREFERRED EMBODIMENTS

Hereinafter, embodiments of the present application are described in detail below with reference to the drawings. Note that the embodiments described in the following are not intended to limit the present application.

In the following description, positional relationships of respective portions are described by setting a three-dimensional global coordinate system. A direction parallel to a first axis of a predetermined plane is referred to as an X-axis direction, a direction parallel to a second axis of the predetermined plane perpendicular to the first axis is referred to as a Y-axis direction, and a direction parallel to a third axis that is perpendicular to both the first axis and the second axis is referred to as a Z-axis direction. The predetermined plane includes an XY plane.

First Embodiment

Figure 1:
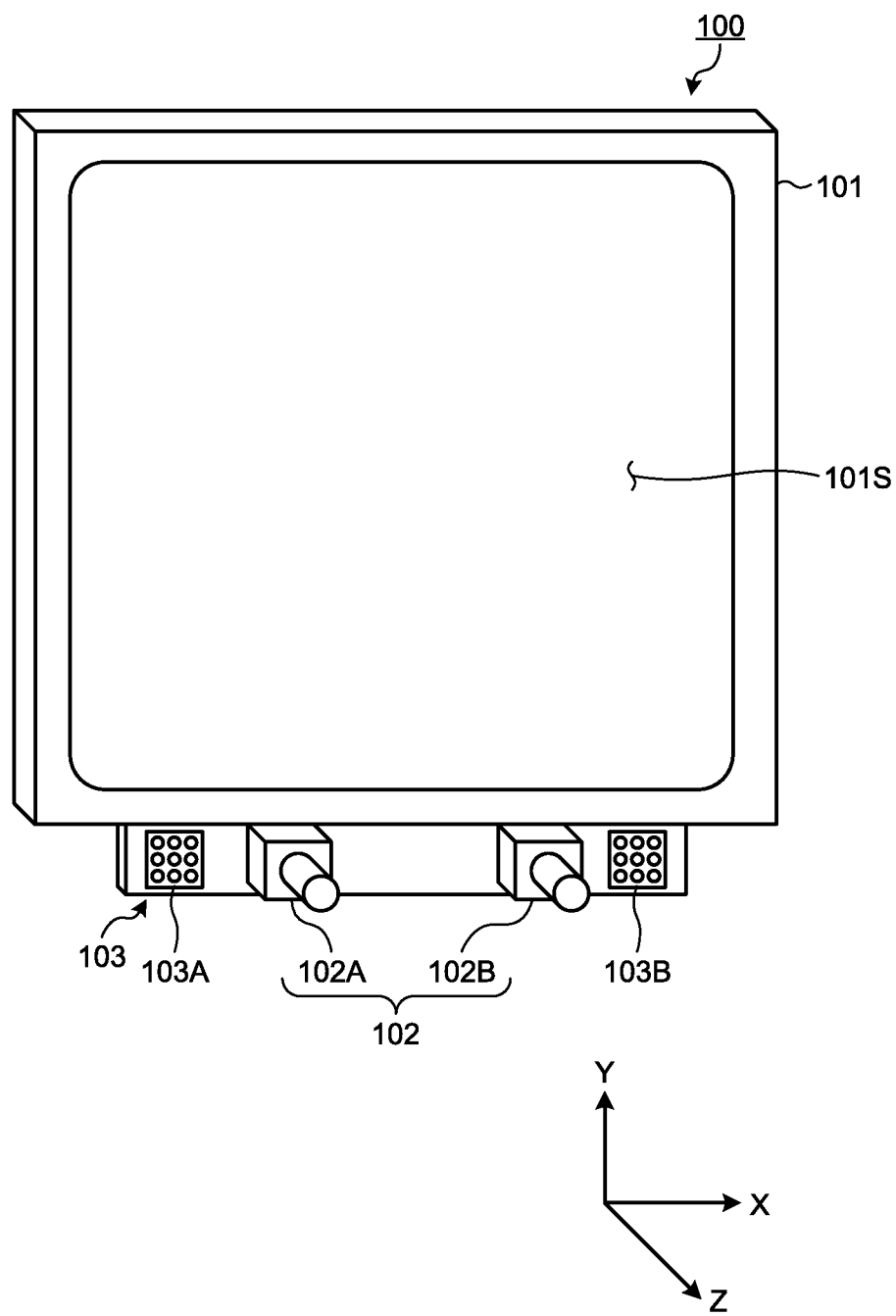
FIG. 1 is a perspective view schematically illustrating an example of an eye tracking device according to a first embodiment.

A first embodiment is described. FIG. 1 is a perspective view schematically illustrating an example of an eye tracking device according to a first embodiment. In the present embodiment, an eye tracking device 100 is a device that detects a line of sight of a subject, and is used also as an estimation device that estimates interest of the subject.

Entire Configuration of Eye Tracking Device

As illustrated in FIG. 1, the eye tracking device 100 includes a display 101, a stereo camera device 102, and an illumination device 103.

The display 101 includes a flat panel display, such as a liquid crystal display (LCD)) or an organic electroluminescence display (OLED). The display 101 functions as a display unit.

In the present embodiment, a display screen 101S of the display 101 is substantially parallel to the XY plane. The X-axis direction is a horizontal direction of the display screen 101S, and the Y-axis direction is a vertical direction of the display screen 101S, and the Z-axis direction is a depth direction perpendicular to the display screen 101S. Moreover, a rightward direction when facing a front of the display screen 101S is a +X direction, and a leftward direction is a −X direction, an upward direction is a +Y direction, a downward direction is a −Y direction, a frontward direction is a +Z direction, and a backward direction is a −Z direction.

The stereo camera device 102 includes a first camera 102A and a second camera 102B serving as an imager. The stereo camera device 102 is arranged below the display screen 101S of the display 101. The first camera 102A and the second camera 102B are arranged in the X-axis direction. The first camera 102A is arranged in the −X direction relative to the second camera 102B. Each of the first camera 102A and the second camera 102B includes an infrared camera, and has an optical system that allows near infrared light having, for example, a wavelength of 850 [nm] to pass through, and an imaging device that can receive the near infrared light.

The illumination device 103 includes a first light source 103A and a second light source 103B serving as a light source. The illumination device 103 is arranged below the display screen 101S of the display 101. The first light source 103A and the second light source 103B are arranged in the X-axis direction. The first light source 103A is arranged in the −X direction relative to the first camera 102A. The second light source 103B is arranged in the +X direction relative to the second camera 102B. Each of the first light source 103A and the second light source 103B includes at least one light emitting diode (LED) light source, and is capable of emitting near infrared light having, for example, a wavelength of 850 [nm]. Note that the first light source 103A and the second light source 103B may be arranged between the first camera 102A and the second camera 102B.

Figure 2:
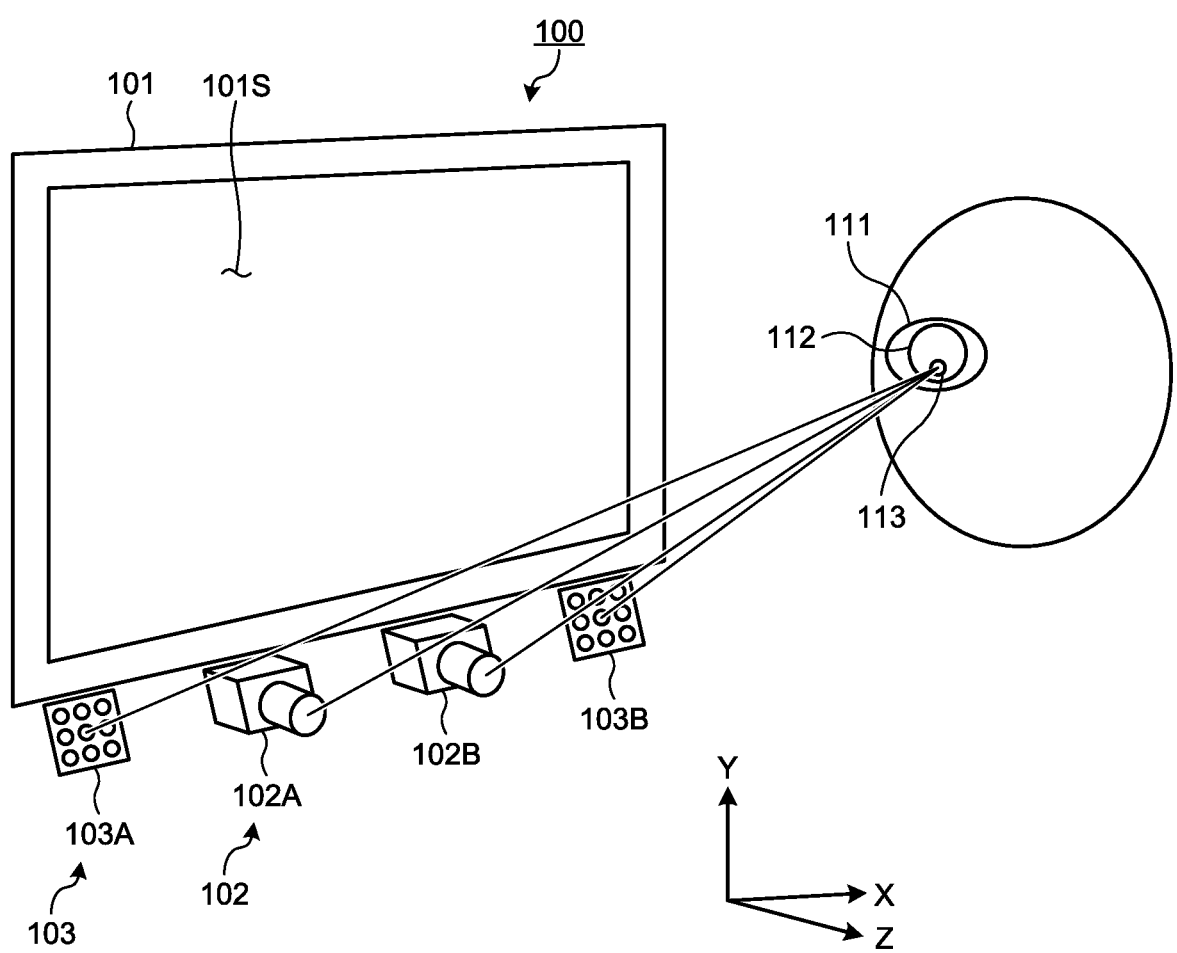
FIG. 2 is a diagram schematically illustrating a positional relationship among a display, a stereo camera device, an illumination device, and an eyeball of a subject according to the present embodiment.

FIG. 2 is a diagram schematically illustrating a positional relationship among a display, a stereo camera device, an illumination device, and an eyeball of a subject according to the present embodiment.

The illumination device 103 emits near infrared light, which is the detection light, to illuminate an eyeball 111 of the subject. The stereo camera device 102 images the eyeball 111 with the second camera 102B when the detection light is emitted from the first light source 103A to be irradiated to the eyeball 111, and images the eyeball 111 with the first camera 102A when the detection light is emitted from the second light source 103B to be irradiated to the eyeball 111.

From at least one of the first camera 102A and the second camera 102B, a frame synchronization signal is output. The first light source 103A and the second light source 103B emit the detection light based on the frame synchronization signal. The first camera 102A acquires image data of the eyeball 111 when the detection light emitted from the second light source 103B is irradiated to the eyeball 111. The second camera 102B acquires image data of the eyeball 111 when the detection light emitted from the first light source 103A is irradiated to the eyeball 111.

When the detection light is irradiated to the eyeball 111, a part of the detection light is reflected on a pupil 112, and the reflected light from the pupil 112 enters the stereo camera device 102. Moreover, when the detection light is irradiated to the eyeball 111, a corneal reflex image 113, which is a virtual image of a cornea, is formed on the eyeball 111, and light from the corneal reflex image enters the stereo camera device 102.

When relative positions among the first camera 102A, the second camera 102B, the first light source 103A, and the second light source 103B are appropriately set, the intensity of light entering the stereo camera device 102 from the pupil 112 becomes low, and the intensity of light entering the stereo camera device 102 from the corneal reflex image 113 becomes high. That is, the image of the pupil 112 acquired by the stereo camera device 102 has low intensity, and the image of the corneal reflex image 113 has high intensity. The stereo camera device 102 can detect a position of the pupil 112 and a position of the corneal reflex image 113 based on the intensity of an acquired image.

Figure 3:
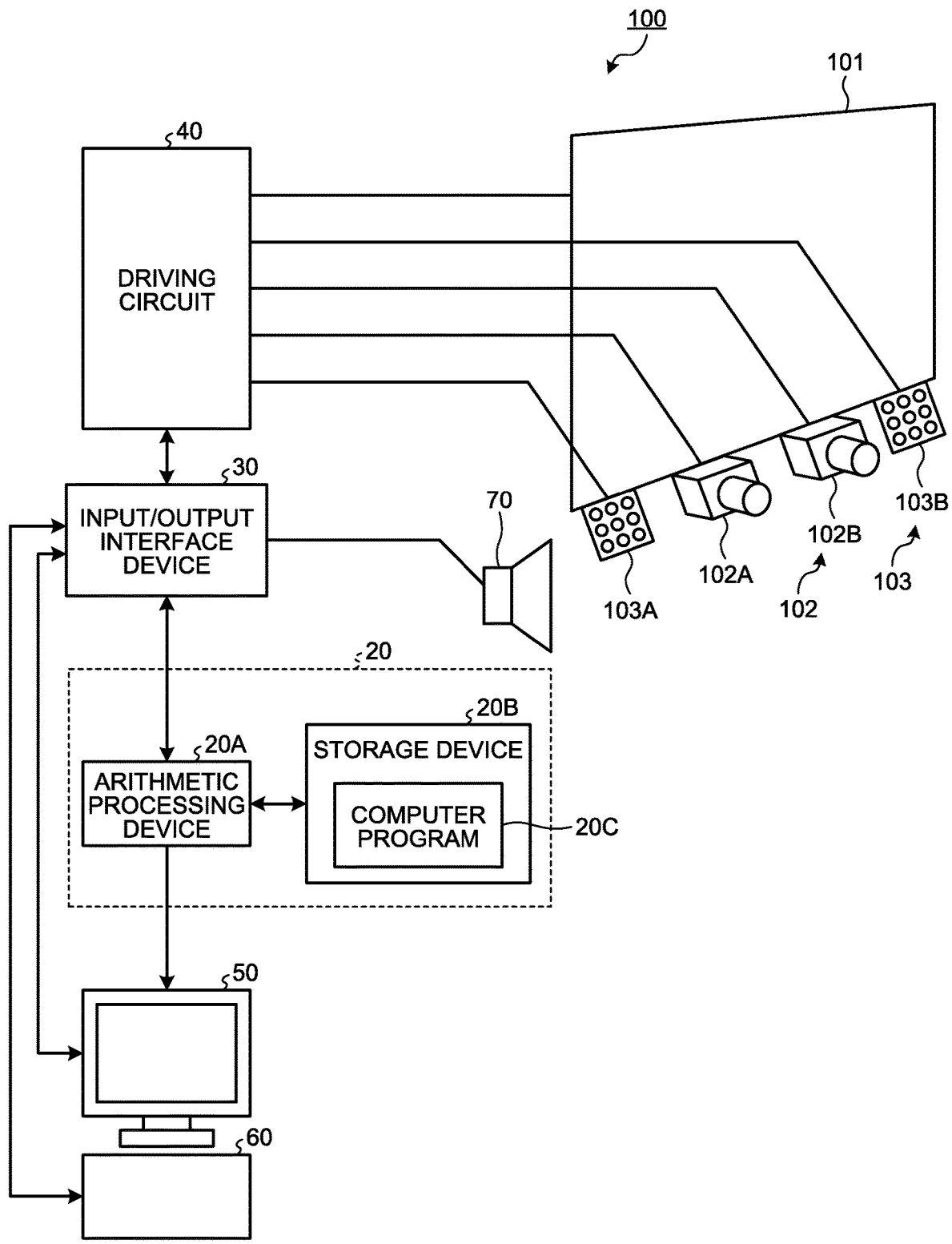
FIG. 3 is a diagram illustrating an example of a hardware configuration of the eye tracking device according to the present embodiment.

FIG. 3 is a diagram illustrating an example of a hardware configuration of the eye tracking device according to the present embodiment. As illustrated in FIG. 3, the eye tracking device 100 includes the display 101, the stereo camera device 102, the illumination device 103, a computer system 20, an input/output interface device 30, a driving circuit 40, an output device 50, an input device 60, and a voice output device 70. The computer system 20 serving as a control unit includes an arithmetic processing device 20A and a storage device 20B.

The computer system 20, the driving circuit 40, the output device 50, the input device 60, and the voice output device 70 perform data communication through the input/output interface device 30.

The arithmetic processing device 20A includes a microprocessor, such as a central processing unit (CPU). The storage device 20B includes a memory or a storage, such as a read-only memory (ROM) and a random access memory (RAM). The arithmetic processing device 20A performs arithmetic processing according to a computer program 20C stored in the storage device 20B.

The driving circuit 40 generates a driving signal, and output it to the display 101, the stereo camera device 102, and the illumination device 103. Moreover, the driving circuit 40 supplies image data of the eyeball 111 acquired by the stereo camera device 102 to the computer system 20 through the input/output interface device 30.

The output device 50 includes a display, such as a flat panel display. Note that the output device 50 may include a printer device. The input device 60 is operated, to thereby generate input data. The input device 60 includes a keyboard or a mouse for a computer system. Note that the input device 60 may include a touch sensor that is arranged on a display screen of the output device 50. The voice output device 70 includes a speaker, and outputs voice, for example, to call attention to the subject.

In the present embodiment, the display 101 and the computer system 20 are separate devices. Note that the display 101 and the computer system 20 may be unified. For example, when the eye tracking device 100 includes a tablet personal computer, the tablet personal computer may be equipped with the computer system 20, the input/output interface device 30, the driving circuit 40, and the display 101.

Figure 4:
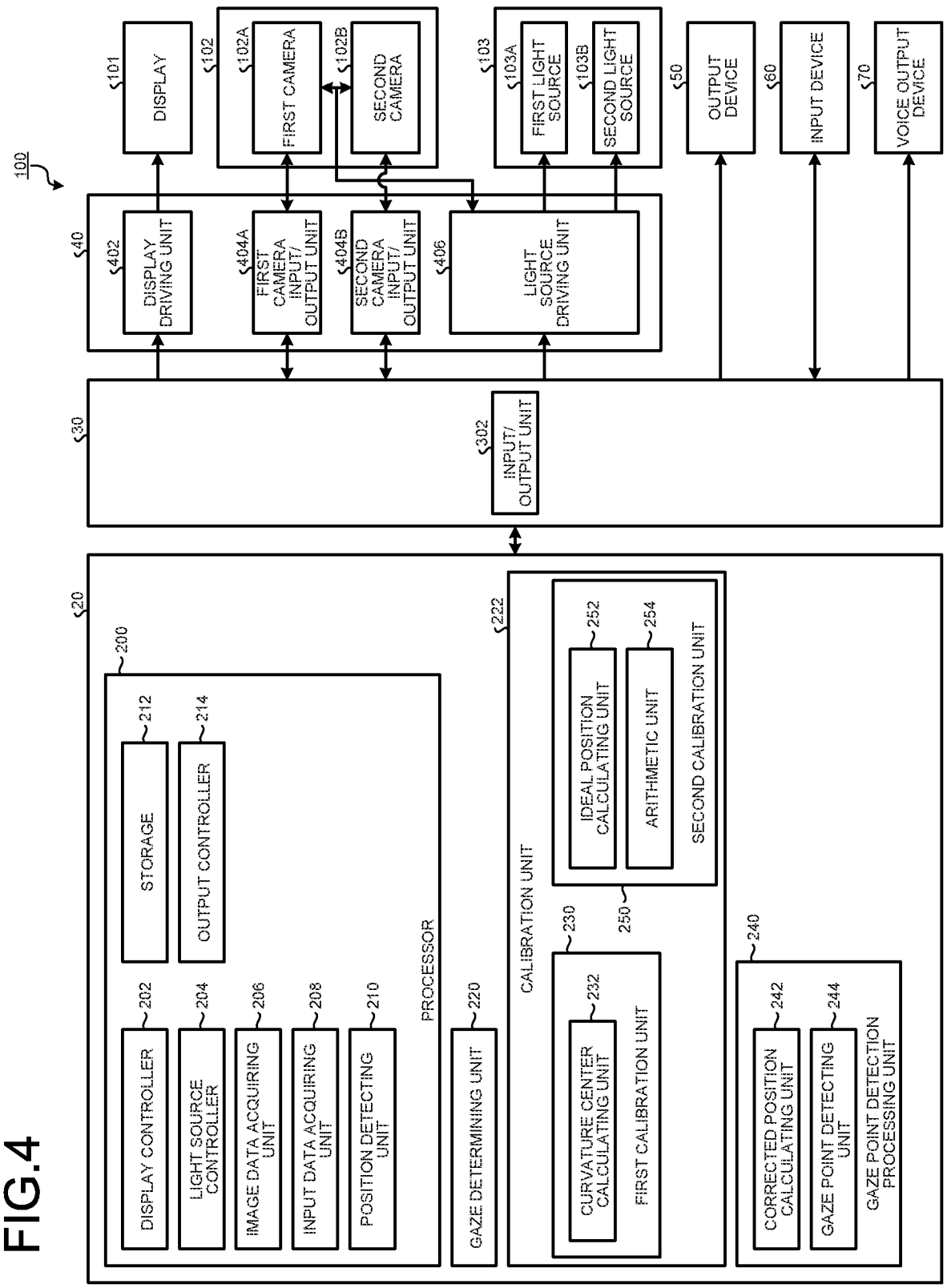
FIG. 4 is a functional block diagram illustrating an example of the eye tracking device according to the present embodiment.

FIG. 4 is a functional block diagram illustrating an example of the eye tracking device according to the present embodiment. As illustrated in FIG. 4, the input/output interface device 30 includes an input output unit 302. The driving circuit 40 includes a display driving unit 402, a first camera input/output unit 404A, a second camera input/output unit 404B, and a light source driving unit 406. The display driving unit 402 generates a driving signal to drive the display 101, and outputs it to the display 101. The first camera input/output unit 404A generates a driving signal to drive the first camera 102A, and outputs it to the first camera 102A. The second camera input/output unit 404B generates a driving signal to drive the second camera 102B, and outputs it to the second camera 102B. The light source driving unit 406 generates a driving signal to drive the first light source 103A and the second light source 103B, and outputs it to the first light source 103A and the second light source 103B. Moreover, the first camera input/output unit 404A supplies image data of the eyeball 111 that is acquired by the first camera 102A to the computer system 20 through the input output unit 302. The second camera input/output unit 404B supplies image data of the eyeball 111 that is acquired by the second camera 102B to the computer system 20 through the input output unit 302.

The computer system 20 controls the eye tracking device 100. The computer system 20 includes a processor 200, a gaze determining unit 220, a calibration unit 222, and a gaze point detection processing unit 240. Functions of the computer system 20 are implemented by the arithmetic processing device 20A and the storage device 20B.

The processor 200 performs various kinds of processing for eye tracking. The processor 200 includes a display controller 202, a light source controller 204, an image data acquiring unit 206, an input data acquiring unit 208, a position detecting unit 210, a storage 212, and an output controller 214.

The display controller 202 displays an image to be shown to the subject on the display screen 101S of the display 101. The display controller 202 can display an image, for example, at one point on the display screen 101S.

The light source controller 204 controls the light source driving unit 406, to control an operating state of the first light source 103A and the second light source 103B. The light source controller 204 controls the first light source 103A and the second light source 103B such that the first light source 103A and the second light source 103B emit the detection light in different timings.

The image data acquiring unit 206 acquires image data of the eyeball 111 of the subject that is acquired by the stereo camera device 102 including the first camera 102A and the second camera 102B from the stereo camera device 102 through the input output unit 302.

The input data acquiring unit 208 acquires input data that is generated as the input device 60 is operated, from the input device 60 through the input output unit 302.

The position detecting unit 210 detects position data of a pupil center based on the image data of the eyeball 111 acquired by the image data acquiring unit 206. Moreover, the position detecting unit 210 detects position data of a corneal reflex center based on the image data of the eyeball 111 acquired by the image-data acquiring unit 206. The pupil center is a center of the pupil 112. The corneal reflex center is a center of the corneal reflex image 113. The position detecting unit 210 detects the position data of the pupil center and the position data of the corneal reflex center for the respective left and right eyeballs 111 of the subject.

The storage 212 and the output controller 214 are described later.

The gaze determining unit 220 performs gaze determination processing by using a result of processing by the processor 200, more specifically, by using the position data of the pupil center and the position data of the corneal reflex center detected by the position detecting unit 210. The gaze determination processing is processing to determine whether the subject gazes at a target position in calibration processing described later.

The calibration unit 222 includes a first calibration unit 230 and a second calibration unit 250. The calibration unit 222 performs, as the calibration processing for eye tracking, first calibration processing by the first calibration unit 230, and second calibration processing by the second calibration unit 250.

The first calibration unit 230 performs the first calibration processing by using a result of processing performed by the processor 200. The first calibration processing is one of calibration processing, and is calibration processing for the gaze-point detection processing described later. Details of the processing are described later. Moreover, the first calibration unit 230 performs the first calibration processing for gaze point detection when the gaze determining unit 220 determines that the subject is gazing at a target position.

The first calibration unit 230 includes a curvature center calculating unit 232. The curvature-center calculating unit 232 calculates a position of a corneal curvature center of the eyeball 111 based on the image data of the eyeball 111 acquired by the image data acquiring unit 206 of the processor 200.

The gaze point detection processing unit 240 performs gaze point detection processing by using a result of processing performed by the processor 200 and a result (calibration data) of processing performed by the first calibration unit 230. The gaze point detection processing is processing to detect a gaze point of the subject. Details of the processing are described later. The gaze point-detection processing unit 240 includes a corrected position calculating unit 242 and a gaze point detecting unit 244.

The corrected position calculating unit 242 corrects the position of the corneal curvature center based on a distance between the center of the pupil 112 detected by the position detecting unit 210 of the processor 200 and the corneal curvature center calculated by the curvature center calculating unit 232 of the first calibration unit 230.

The gaze point detecting unit 244 detects a position of a gaze point of the subject based on the image data of the eyeball 111 that is acquired by the image data acquiring unit 206 of the processor 200. In the present embodiment, the position of a gaze point is a position of an intersection of a line-of-sight vector of the subject and the display screen 101S of the display 101 defined by the three dimensional global coordinate system. The gaze point detecting unit 244 detects a line-of-sight vector that is a direction of sight of the eyeball 111 of each of the left and right eyeballs 111 of the subject based on the position of the pupil center and the corneal curvature center acquired from the image data of the eyeball 111. That is, the gaze point detecting unit 244 is also a line-of-sight detecting unit that detects a direction of the line of sight of each of the left and right eyeballs 111 of the subject. After detecting the line-of-sight vector of each of the left and right eyeballs 111 of the subject, the gaze-point detecting unit 244 detects a position of a gaze point indicating an intersection of the line-of-sight vector and the display screen 101S.

The second calibration unit 250 performs the second calibration processing by using a result of processing performed by the processor 200 and a result of processing performed by the gaze point detection processing unit 240. The second calibration processing is one of calibration processing, and is calibration processing for the subsequent gaze point detection processing. Details of the processing are described later. Moreover, the second calibration unit 250 performs the second calibration processing for the subsequent gaze point detection processing when the gaze determining unit 220 determines that the subject is gazing at the target position.

The second calibration unit 250 includes an ideal position calculating unit 252 and an arithmetic unit 254. The ideal position calculating unit 252 calculates an ideal corneal curvature center of each of left and right eyeballs from a position of the image displayed at one point on the display screen 101S and the position of the center of the pupil 112.

The arithmetic unit 254 calculates a position difference that is a difference between a position of a corrected corneal curvature center calculated by the corrected position calculating unit 242 of the gaze point detection processing unit 240 and a position of the ideal corneal curvature center calculated by the ideal position calculating unit 252 for each of the left and right eyeballs.

Furthermore, the storage 212 of the processor 200 stores an eye tracking program that causes a computer to perform processing of displaying an image at one point on the display screen 101S of the display 101, processing of irradiating near infrared light from the light source to left and right eyeballs of a subject, processing of acquiring image data of the left and right eyeballs of the subject to which the near infrared light is irradiated, processing of detecting a position of a pupil center indicating a center of the pupil 112 and a position of a corneal reflex image 113 of each of the left and right eyeballs from the acquired image data, processing of determining whether the subject is gazing at a target position in the calibration processing by using position data of the pupil center and position data of the corneal reflex center, processing of calculating a position of a corneal curvature center of each of the left and right eyeballs based on a virtual straight line connecting the light source and the corneal reflex center and a virtual straight line connecting the image and the pupil center, processing of correcting the position of the corneal curvature center based on a distance between the pupil center and the corneal curvature center to calculate a position of the corrected corneal curvature center of each of the left and right eyeballs, processing of detecting a gaze point of each of the left and right eyeballs from the position of the pupil center and the position of the corrected corneal curvature center, processing of calculating a position of an ideal corneal curvature center of each of the left and right eyeballs from the position of the image displayed at one point on the display screen 101S and the position of the pupil center, and processing of calculating a position difference that is a difference between the position of the corrected corneal curvature center and the position of the ideal corneal curvature center for each of the left and right eyeballs.

The output controller 214 outputs data to at least one of the display 101, the output device 50, and the voice output device 70. In the present embodiment, the output controller 214 displays an image at one point on the display screen 101S. Moreover, the output controller 214 displays a position of a gaze point of each of the left and right eyeballs 111 of the subject on the display screen 101S or the output device 50.

The computer system 20 has the configuration as described above.

Overview of Method of Calculating Corneal Curvature Center

Next, an overview of processing of the curvature center calculating unit 232 included in the first calibration unit 230 according to the present embodiment is described. The curvature center calculating unit 232 calculates a position of a corneal curvature center of the eyeball 111 based on image data of the eyeball 111.

Figure 5:
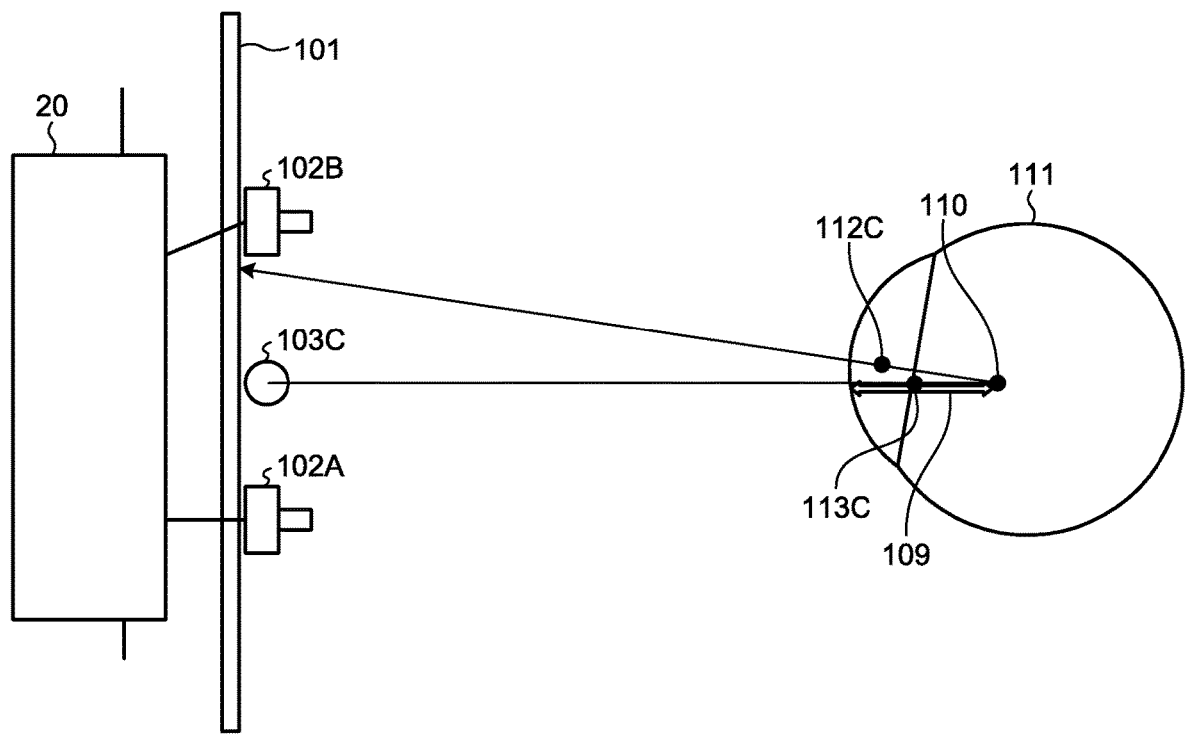
FIG. 5 is a diagram for explaining a method of calculating a position of a corneal curvature center according to the present embodiment.
Figure 6:
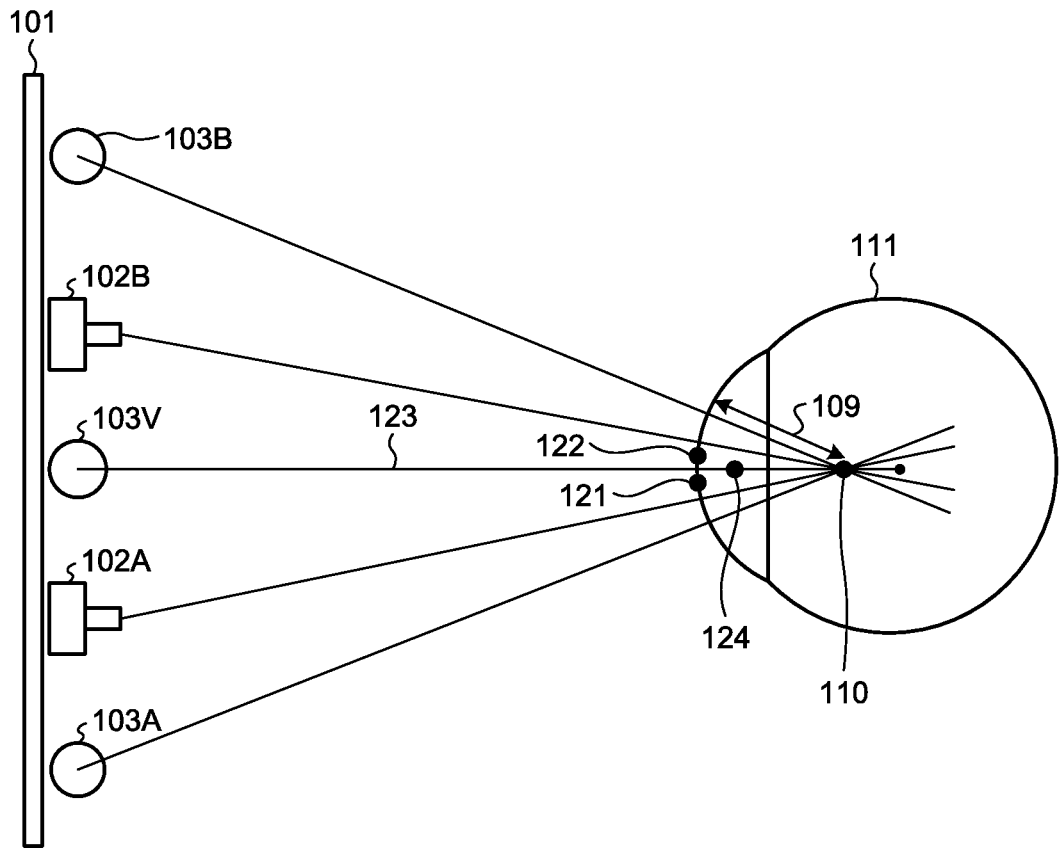
FIG. 6 is a schematic diagram for explaining a method of calculating a position of the corneal curvature center according to the present embodiment.

FIG. 5 and FIG. 6 are schematic diagrams for explaining a method of calculating a position of the corneal curvature center according to the present embodiment. FIG. 5 illustrates an example in which the eyeball 111 is illuminated by one light source 103C. FIG. 6 illustrates an example in which the eyeball 111 is illuminated by the first light source 103A and the second light source 103B.

First, the example in FIG. 5 is described. The light source 103C is arranged between the first camera 102A and the second camera 102B. A pupil center 112C is a center of the pupil 112 (see FIG. 2). A corneal reflex center 113C is a center of the corneal reflex image 113 (see FIG. 2). In FIG. 5, the pupil center 112C indicates a pupil center when the eyeball 111 is illuminated by the one light source 103C. The corneal reflex center 113C indicates a corneal reflex center when the eyeball 111 is illuminated by the one light source 103C.

The corneal reflex center 113C is present on a straight line connecting the light source 103C and a corneal curvature center 110. A corneal curvature radius 109 is a distance between a corneal surface and the corneal curvature center 110.

A position of the corneal reflex center 113C is detected by the stereo camera device 102. The corneal curvature center 110 is present on a straight line connecting the light source 103C and the corneal reflex center 113C. The curvature center calculating unit 232 calculates a position at which a distance from the corneal reflex center 113C on the straight line becomes a predetermined value as the position of the corneal curvature center 110. The predetermined value is a value determined in advance from a general curvature radius value of a cornea, or the like, and is stored in the storage 212.

Next, the example in FIG. 6 is described. In the present embodiment, the first camera 102A and the second light source 103B, and the second camera 102B and the first light source 103A are arranged at bilaterally symmetrical positions relative to a straight line passing through a middle position between the first camera 102A and the second camera 102B. It can be regarded that a virtual light source 103V is present at the middle position between the first camera 102A and the second camera 102B.

A corneal reflex center 121 indicates a corneal reflex center in an image obtained by imaging the eyeball 111 by the second camera 102B. A corneal reflex center 122 indicates a corneal reflex center in an image obtained by imaging the eyeball 111 by the first camera 102A. A corneal reflex center 124 indicates a corneal reflex center corresponding to the virtual light source 103V.

A position of the corneal reflex center 124 is calculated based on a position of the corneal reflex center 121 and a position of the corneal reflex center 122 acquired by the stereo camera device 102. The stereo camera device 102 detects the position of the corneal reflex center 121 and the corneal reflex center 122 in a three dimensional local coordinate system defined for the stereo camera device 102. For the stereo camera device 102, camera calibration by stereo calibration method is performed, and a conversion parameter to convert a three-dimensional local coordinate system of the stereo camera device into a three dimensional global coordinate system is calculated. The conversion parameter is stored in the storage 212.

The curvature center calculating unit 232 converts the position of the corneal reflex center 121 and the position of the corneal reflex center 122 acquired by the stereo camera device 102 into positions in the three dimensional global coordinate system by using the conversion parameter. The curvature center calculating unit 232 calculates a position of the corneal reflex center 124 in the three dimensional global coordinate system based on the position of the corneal reflex center 121 and the position of the corneal reflex center 122 defined by the three dimensional global coordinate system.

The corneal curvature center 110 is present on a straight line 123 connecting the virtual light source 103V and the corneal reflex center 124. The curvature center calculating unit 232 calculates a position at which a distance from the corneal reflex center 124 on the straight line 123 becomes a predetermined value as a position of the corneal curvature center 110. The predetermined value is a value determined in advance from a general curvature radius value of a cornea.

As described, also when two light sources are used, the corneal curvature center 110 is calculated by a method similar to the method in the case in which a single light source is used.

The corneal curvature radius 109 is a distance between a corneal surface and the corneal curvature center 110. Therefore, by calculating a position of the corneal surface and the corneal curvature center 110, the corneal curvature radius 109 is calculated.

Eye Tracking Method

Figure 7:
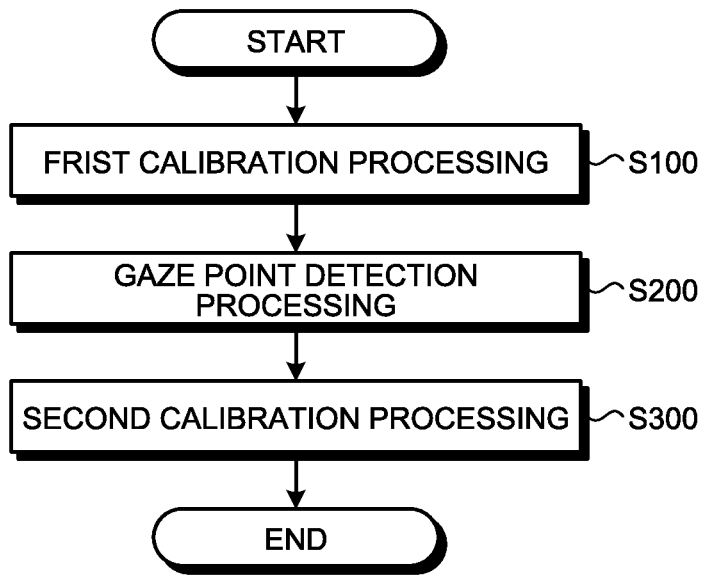
FIG. 7 is a flowchart illustrating an example of the eye tracking method according to the present embodiment.

Next, an example of an eye tracking method according to the present embodiment is described. FIG. 7 is a flowchart illustrating an example of the eye tracking method according to the present embodiment. In the present embodiment, a first calibration processing (step S100), a gaze point detection processing (step S200), and a second calibration processing (step S300) are performed. The first calibration processing includes a gaze determination processing to determine whether a subject is gazing at a target position, a calculation processing of a position of the corneal curvature center 110, and a calculation processing of distance data between the pupil center 112C and the corneal curvature center 110. The second calibration processing includes the gaze determination processing to determine whether the subject is gazing at a target point, and a calculation processing of a position of the ideal corneal curvature center 110. Note that the gaze determination processing is processing included in both of the first calibration processing and the second calibration processing, but can be performed separately from the first calibration processing and the second calibration processing. Moreover, the gaze determination processing may be performed in at least one of the first calibration processing and the second calibration processing.

First Calibration Processing

The first calibration processing (step S100) is described. In the first calibration processing, the display controller 202 sets a target position to be gazed at by the subject. The target position is defined in the three dimensional global coordinate system. In the present embodiment, the display controller 202 sets the target position, for example, at a center position of the display screen 101S of the display 101. Note that the target position may be set at a position of an end portion of the display screen 101S. The display controller 202 displays a target image at the set target position. Thus, the subject is more likely to gaze at the target position.

In the first calibration processing, after the target image is displayed at the target position, an image of the eyeball 111 of the subject is captured by the stereo camera device 102, and the image data acquiring unit 206 acquires the captured image data The position detecting unit 210 detects the position of the pupil center 112C and the position of the corneal reflex center 124 based on the captured image data.

In the first calibration processing, the gaze determining unit 220 performs the gaze determination processing, and determines whether the subject is gazing at the target position based on the position of the pupil center 112C and the position of the corneal reflex center 124 detected by the position detecting unit 210. Hereinafter, the processing performed by the gaze determining unit 220 is described.

Figure 8A:
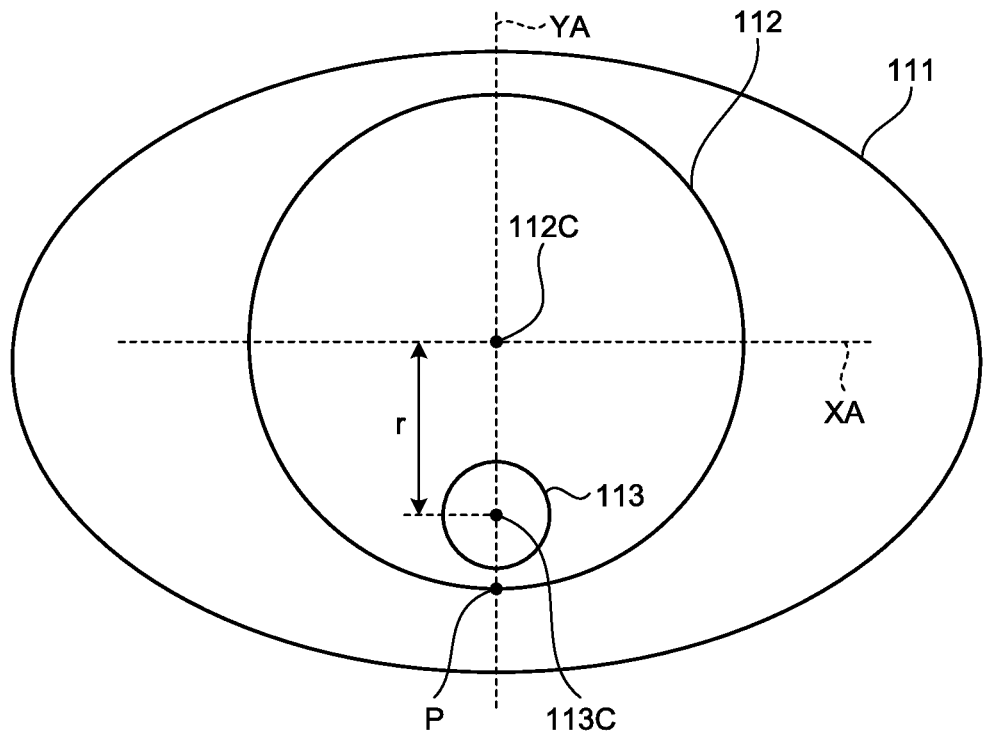
FIG. 8A is an explanatory diagram for explaining gaze determination processing.
Figure 8B:
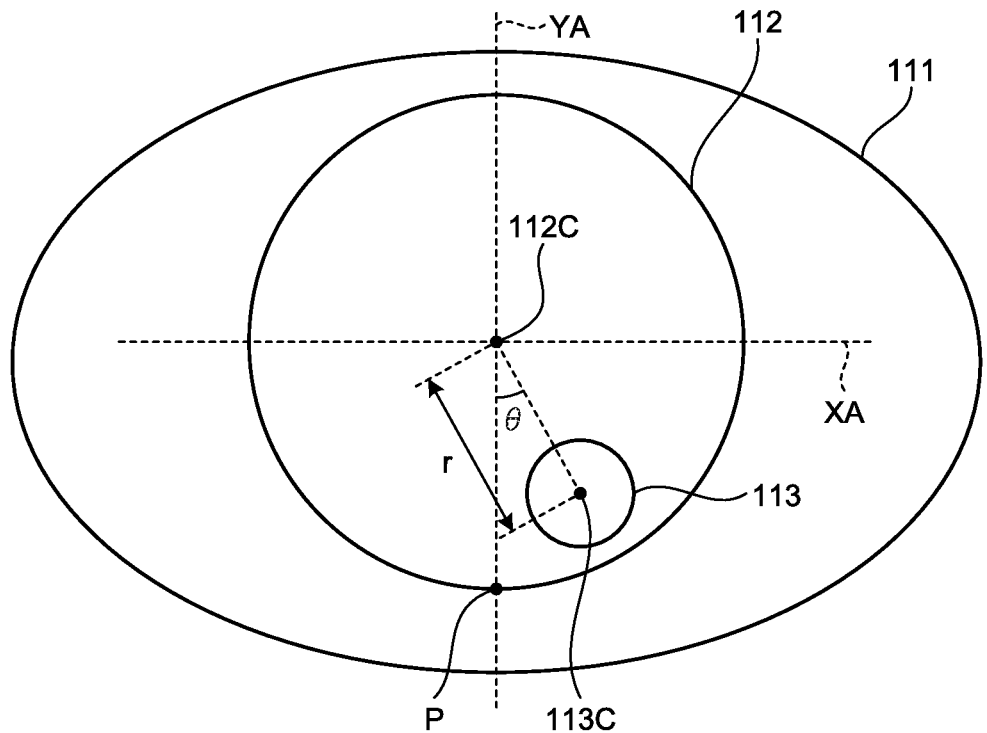
FIG. 8B is an explanatory diagram for explaining the gaze determination processing.

FIG. 8A and FIG. 8B are explanatory diagrams for explaining the gaze determination processing. FIG. 8A and FIG. 8B are schematic diagrams of an image of the eyeball 111 of the subject. A line segment XA in FIG. 8A and FIG. 8B is a virtual straight line along a horizontal direction passing through the pupil center 112C. A line segment YA is a virtual straight line passing through the pupil center 112C and perpendicular to the line segment XA, and along a vertical direction.

FIG. 8A illustrates an example of an image of the eyeball 111 when the subject is positioned at a standard position relative to the display 101, and when the subject gazes at the target position located at the center position on the display screen 101S. The standard position is a position in front (+Z direction) of the display 101, and is a position that is determined in advance for the subject to be positioned for performing the eye tracking.

As illustrated in FIG. 8A, when the subject is gazing at the target position located at the center position, the corneal reflex image 113 is positioned near the line segment YA ideally. Moreover, in the present embodiment, because the stereo camera device 102 is positioned below (in the −Y direction) the display screen 101S, the corneal reflex image 113 and the corneal reflex center 113C are positioned on a lower side (in the −Y direction) of the pupil center 112C. A distance between the pupil center 112C and the corneal reflex center 113C is referred to as a distance r. The distance r decreases when the subject looks at a lower side (in the −Y direction) of the display screen 101S, and increases when the subject looks at an upper side (in the +Y direction) of the display screen 101S. Moreover, the distance r when the subject is gazing at an upper side (in the +Y direction) relative to the target position located at the center position becomes longer than the distance r when the subject is gazing at the target position at the center position.

Furthermore, FIG. 8B illustrates an example of an image when the subject is gazing at an upper right portion relative to the center position on the display screen 101S. An arbitrary virtual point on the line segment YA is referred to as a reference point P. Moreover, an angle formed between a straight line connecting the pupil center 112C and the reference point P (a line segment YA herein) and a straight line connecting the pupil center 112C and the corneal reflex center 113C is referred to as an angle θ. In FIG. 8A, since the corneal reflex center 113C is positioned on the line segment YA, the angle θ is 0 degree. In FIG. 8B, since the subject is gazing at an upper right portion relative to the target position, the position of the corneal reflex center 113C is shifted to a right side from the line segment YA, and the angle θ is larger than 0 degree.

From the above point of view, the gaze determining unit 220 calculates the distance r and the angle θ from the position of the pupil center 112C and the position of the corneal reflex center 124. The gaze determining unit 220 determines whether the subject is gazing at the target position based on the calculated distance r and angle θ.

Specifically, the gaze determining unit 220 reads a distance threshold r0 determined in advance from the storage 212. The distance threshold r0 is a numeric range (distance range) having a lower limit and an upper limit. The gaze determining unit 220 checks whether the calculated distance r falls within the distance threshold r0, and thereby determines whether the subject is gazing at the target position. The gaze determining unit 220 determines that that the subject is gazing at the target position when the calculated distance r falls within the distance threshold r0, and determines that the subject is not gazing at the target position when the calculated distance r falls outside the distance threshold r0. The distance threshold r0 is a numeric range determined in advance and, for example, since the corneal curvature radiuses of human is approximately uniform, it is possible to be set as a fixed value, and it is preferable to be within a range between 3 mm and 5 mm.

Moreover, the gaze determining unit 220 reads an angle threshold θ0 that is set in advance from the storage 212. The angle threshold θ0 is a preset single value. The gaze determining unit 220 checks whether the calculated angle θ is equal to or smaller than the angle threshold θ0, and thereby determines whether the subject is gazing at the target position. The gaze determining unit 220 determines that the subject is gazing at the target position when the calculated angle θ is equal to or smaller than the angle threshold θ0, and determines that the subject is not gazing at the target position when the calculated angle θ is larger than the angle threshold θ0. The angle threshold θ0 is a value set in advance an, for example, it is preferable to be a value equal to or larger than 20° and equal to or smaller than 30°. Note that the reference point P is a point set to be positioned on the line segment YA in the present embodiment, but a position for the reference point P is arbitrarily set. Furthermore, the gaze determining unit 220 may set the angle threshold θ0 to a numeric range (angle range) having an upper limit and a lower limit. In this case, the gaze determining unit 220 determines that the subject is gazing at the target position when the angle θ is equal to or smaller than the angle threshold θ0 (or within the range of the angle threshold θ0), and determines that the subject is not gazing at the target position when the angle θ is larger than the angle threshold θ0 (or outside the range of the angle threshold θ0).

More specifically, the gaze determining unit 220 determines that the subject is gazing at the target position when the calculated distance r falls within the range of the distance threshold r0 and the calculated angle θ is equal to or smaller than the angle threshold θ0. Moreover, the gaze determining unit 220 determines that the subject is not gazing at the target position when at least one of a case in which the calculated distance r falls outside the range of the distance threshold r0, and a case in which the calculated angle θ is larger than the angle threshold θ0 is satisfied. As described, the gaze determining unit 220 determines whether the subject is gazing at the target position based on both the distance r and the angle θ. Note that the gaze determining unit 220 may determine whether the subject is gazing at the target position based on only one of the distance r and the angle θ. That is, the gaze determining unit 220 only has to set at least one index value indicating a relationship between the position of the pupil center 112C and the position of the corneal reflex center 113C. Thus, the gaze determining unit 220 may determine that the subject is gazing at the target position when this index value falls within a range of a predetermined threshold, and determine that the subject is not gazing at the target position when this index value falls outside the range of the threshold. The index value is at least one of the distance r and the angle θ in the example of the present embodiment, but it is not limited to the distance r and the angle θ as long as it is a value indicating the relationship between the position of the pupil center 112C and the position of the corneal reflex center 113C.

The gaze determining unit 220 determines whether the subject is gazing at the target position by performing the gaze determination processing as described above. When the gaze determining unit 220 determines that the subject is gazing at the target position, the first calibration unit 230 (the curvature center calculating unit 232) performs the calibration processing based on the image captured by the stereo camera device 102. The first calibration unit 230 (the curvature center calculating unit 232) performs calculation processing of a position of the corneal curvature center 110 and calculation processing of distance data between the pupil center 112C and the corneal curvature center 110 as the calibration processing.

Figure 9:
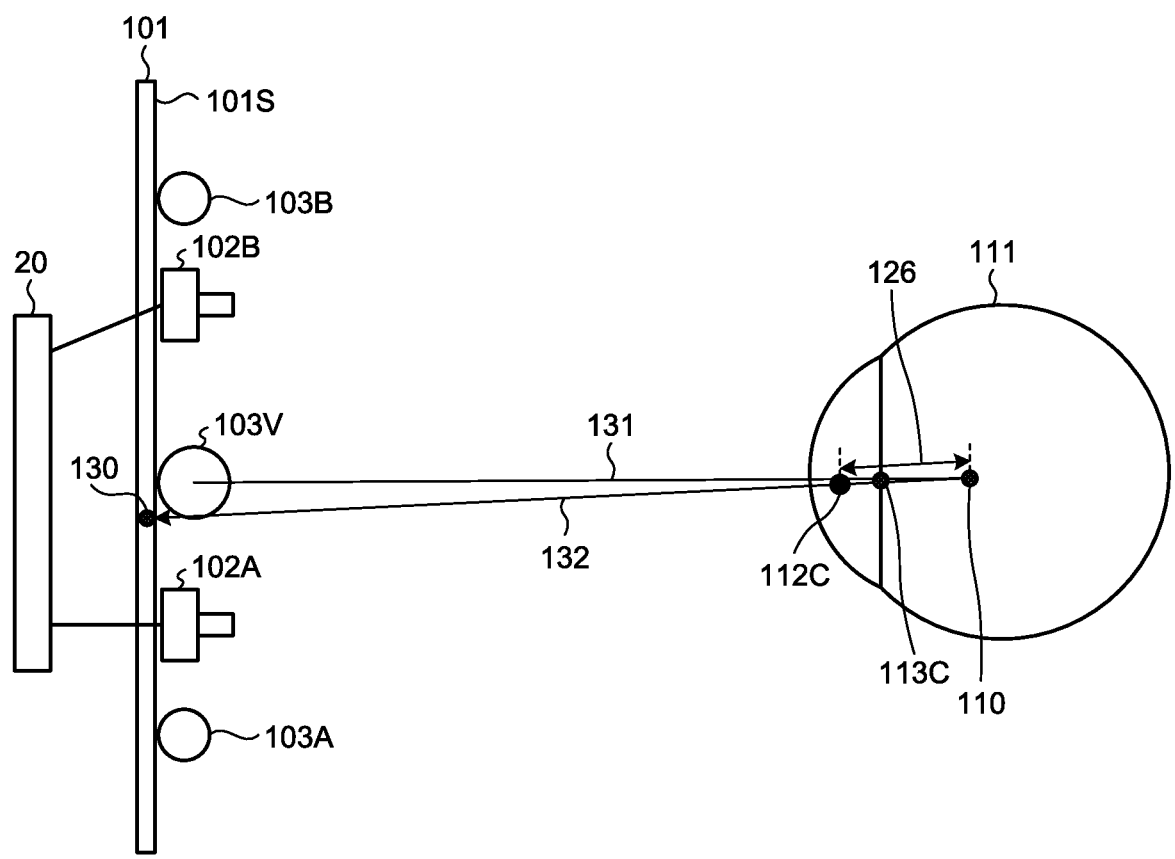
FIG. 9 is a schematic diagram for explaining an example of calibration processing performed by a first calibration unit according to the present embodiment.

FIG. 9 is a schematic diagram for explaining an example of the calibration processing performed by the first calibration unit according to the present embodiment. As illustrated in FIG. 9, the display controller 202 sets a target position 130 to be gazed at by the subject. The target position 130 is defined in the three dimensional global coordinate system.

In the present embodiment, the target position 130 is set, for example, at a center position of the display screen 101S of the display 101. Note that the target position 130 may be set at a position of an end portion of the display screen 101S.

The display controller 202 displays a target image at the set target position 130. Thus, the subject is more likely to gaze at the target position 130.

A straight line 131 is a straight line connecting the virtual light source 103V and the corneal reflex center 113C. A straight line 132 is a straight line connecting the target position 130 and the pupil center 112C. The corneal curvature center 110 is an intersection of the straight line 131 and the straight line 132. The curvature center calculating unit 232 can calculate a position of the corneal curvature center 110 based on the position of the virtual light source 103V, the position of the target position 130, the position of the pupil center 112C, and the corneal reflex center 113C.

Figure 10:
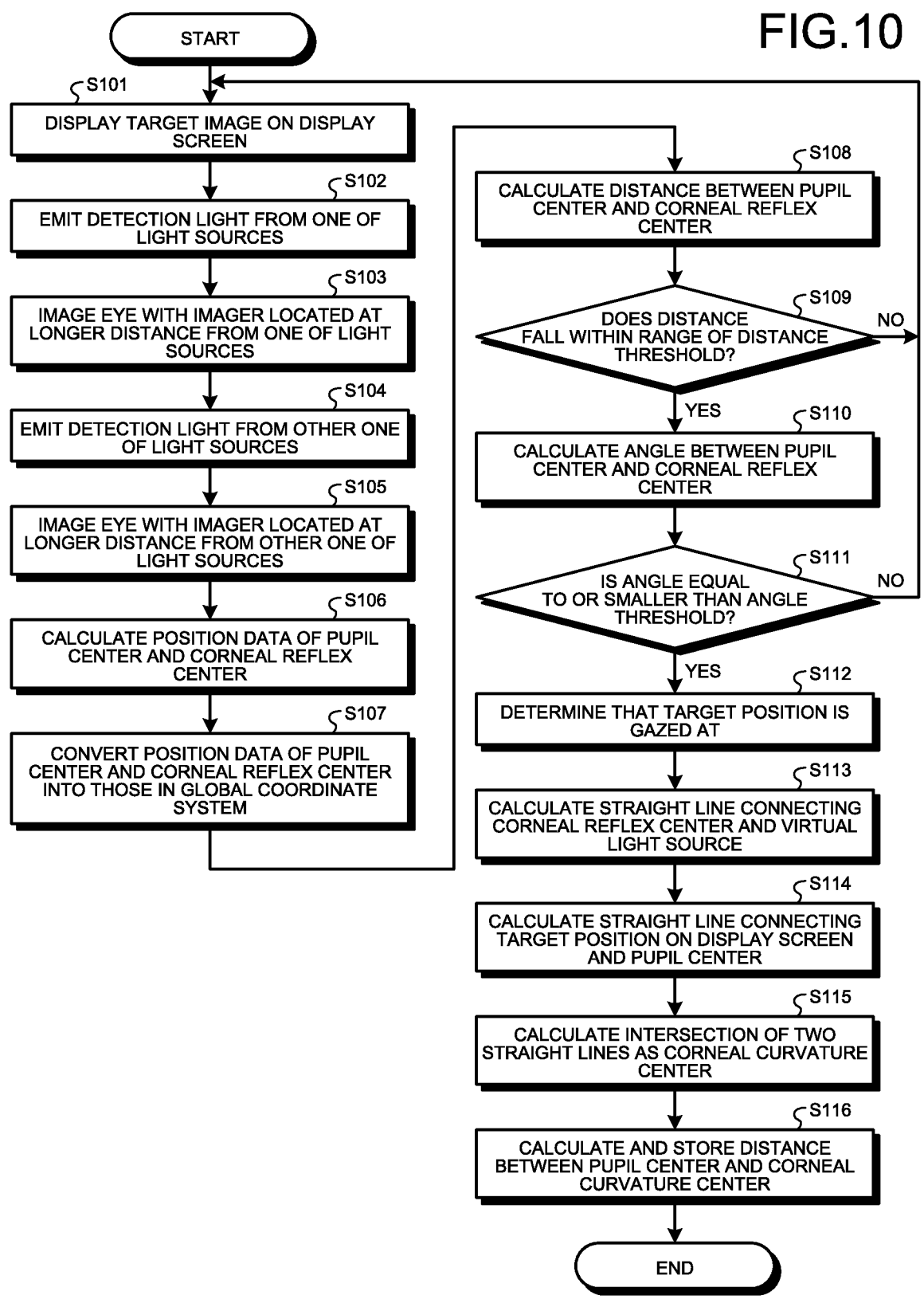
FIG. 10 is a flowchart illustrating an example of first calibration processing according to the present embodiment.

Hereinafter, a flow of the first calibration processing is described based on a processing flow of the first calibration processing. FIG. 10 is a flowchart illustrating an example of the first calibration processing according to the present embodiment. The display controller 202 displays a target image on the display screen 101S of the display 101 (step S101). The subject can gaze at the target position 130 by gazing at the target image.

Next, the light source controller 204 controls the light source driving unit 406 to emit the detection light from one of the light sources among the first light source 103A and the second light source 103B (step S102). The stereo camera device 102 images an eye of the subject with a camera located at a longer distance from the light source from which the detection light is emitted among the first camera 102A and the second camera 102B (step S103).

Next, the light source controller 204 controls the light source driving unit 406 to emit the detection light from the other one of the light sources among the first light source 103A and the second light source 103B (step S104). The stereo camera device 102 images an eye of the subject with a camera located at a longer distance from the light source from which the detection light is emitted among the first camera 102A and the second camera 102B (step S105).

The pupil 112 is detected by the stereo camera device 102 as a dark portion, and the corneal reflex image 113 is detected by the stereo camera device 102 as a bright portion. That is, an image of the pupil 112 acquired by the stereo camera device 102 becomes a low intensity image, and an image of the corneal reflex image 113 becomes a high intensity image. The position detecting unit 210 can detect a position of the pupil 112 and the position of the corneal reflex image 113 based on the intensity of the captured image. Moreover, the position detecting unit 210 calculates the position of the pupil center 112C based on image data of the pupil 112. Furthermore, the position detecting unit 210 detects a position of the corneal reflex center 113C based on image data of the corneal reflex image 113 (step S106).

The position detected by the stereo camera device 102 is a position defined by the three dimensional local coordinate system. The position detecting unit 210 performs coordinate conversion of the position of the pupil center 112C and the position of the corneal reflex center 113C detected by the stereo camera device 102 by using conversion parameter stored in the storage 212, to calculate a position of the pupil center 112C and a position of the corneal reflex center 113C defined by the three dimensional global coordinate system (step S107).

After the position of the pupil center 112C and the position of the corneal reflex center 113C are calculated, the gaze determining unit 220 performs the gaze determination processing from step S108 to step S112. The gaze determining unit 220 calculates the distance r between the pupil center 112C and the corneal reflex center 113C based on the position data of the pupil center 112C and the position data of the corneal reflex center 113C (step S108). The gaze determining unit 220 checks whether the calculated distance r falls within the range of the distance threshold r0 (step S109), and when the distance r falls within the range of the distance threshold r0 (step S109: YES), calculates the angle θ between the pupil center 112C and the corneal reflex center 113C (step S110). Next, the gaze determining unit 220 checks whether the calculated angle θ is equal to or smaller than the angle threshold θ0 (step S111), and when the angle θ is equal to or smaller than the angle threshold θ0 (step S111: YES), determines that the subject is gazing at the target position (step S112).

When the distance r does not fall within the range of the distance threshold r0 (step S109: NO), that is, when the distance r falls outside the range of the distance threshold r0, the gaze determining unit 220 determines that the subject is not gazing at the target position, and invalidates the acquired data (the position data of the pupil center 112C and the position data of the corneal reflex center 113C), and returns to step S101 to perform the next imaging. In this case, the gaze determining unit 220 may return to step S101, for example, after notifying the operator or the subject that the target position is not gazed at. After returning back to step S101, the target image is displayed at the target position 130, an image of the eyeball 111 is newly imaged to calculate a position of the pupil center 112C and a position of the corneal reflex center 113C, and the gaze determination processing is again performed. When the angle θ is not equal to or smaller than the angle threshold θ0 (step S110: NO), that is, when the angle θ is larger than the angle threshold θ0 also, the gaze determining unit 220 determines that the subject is not gazing at the target position, invalidates the acquired calibration data acquired, returns to step S101 to perform the next imaging, and performs the gaze determination processing with the next image.

When the gaze determining unit 220 determines that the subject is gazing at the target position, the curvature center calculating unit 232 calculates the straight line 131 connecting the corneal reflex center 113C defined by the global coordinate system and the virtual light source 103V (step S113).

Next, the curvature center calculating unit 232 calculates the straight line 132 connecting the target position 130 set on the display screen 101S of the display 101 and the pupil center 112C (step S114). The curvature center calculating unit 232 acquires an intersection of the straight line 131 calculated at step S113 and the straight line 132 calculated at step S114, and determines this intersection as the corneal curvature center 110 (step S115).

Thereafter, the curvature center calculating unit 232 calculates a distance 126 between the pupil center 112C and the corneal curvature center 110, and stores it in the storage 212 (step S116). The stored distance is used to calculate the corneal curvature center 110 in the gaze point detection at step S200. At step S116, the first calibration processing is ended.

Gaze Point Detection Processing

Next, the gaze point detection processing (step S200) is described. The gaze point detection processing is performed after the first calibration processing by the gaze point-detection processing unit 240. The gaze point detecting unit 244 of the gaze point detection processing unit 240 calculates a line-of-sight vector and a position of a gaze point of the subject based on image data of the eyeball 111.

Figure 11:
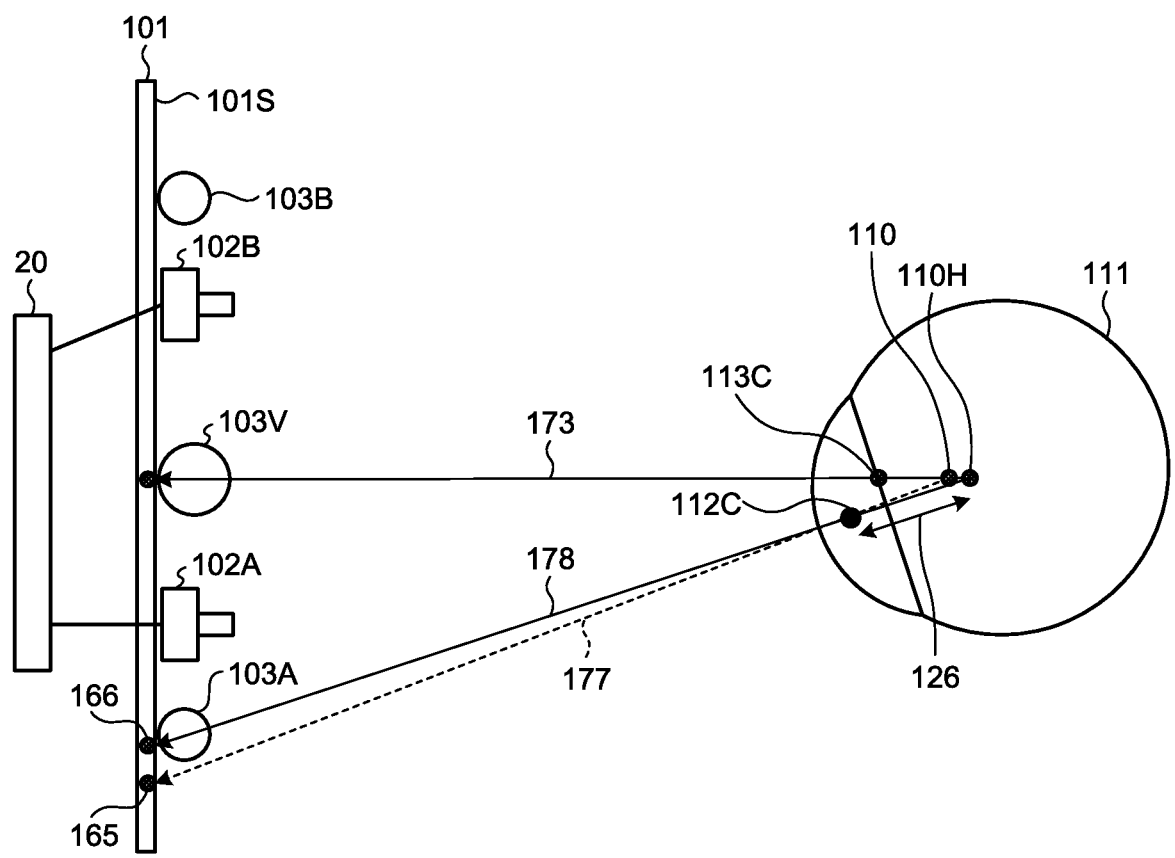
FIG. 11 is a schematic diagram for explaining an example of gaze-point detection processing according to the present embodiment.

FIG. 11 is a schematic diagram for explaining an example of the gaze point detection processing according to the present embodiment. The gaze point detection processing includes correction of a position of the corneal curvature center 110 by using the distance 126 between the pupil center 112C and the corneal curvature center 110 acquired in the first calibration processing (step S100), and calculation of a gaze point by using a corrected position of the corneal curvature center 110.

In FIG. 11, a gaze point 165 indicates a gaze point that is acquired from the corneal curvature center 110 calculated by using a general curvature radius value. A gaze point 166 indicates a gaze point that is acquired from a corneal curvature center 110H calculated by using the distance 126 acquired in the first calibration processing.

The pupil center 112C indicates a pupil center that is calculated in the first calibration processing, and the corneal reflex center 113C indicates a corneal reflex center that is calculated in the first calibration processing.

A straight line 173 is a straight line connecting the virtual light source 103V and the corneal reflex center 113C. The corneal curvature center 110 is a position of a corneal curvature center calculated from a general curvature radius value.

The distance 126 is a distance between the pupil center 112C and the corneal curvature center 110 calculated by the first calibration processing.

The corneal curvature center 110H indicates a position of a corrected corneal curvature center obtained by correcting the corneal curvature center 110 by using the distance 126.

The corneal curvature center 110H is acquired based on that the corneal curvature center 110 is present on the straight line 173, and that the distance between the pupil center 112C and the corneal curvature center 110 is the distance 126. Thus, a line-of-sight 177 that is calculated when a general curvature radius value is used is corrected to a line-of-sight 178. Moreover, the gaze point on the display screen 101S of the display 101 is corrected from the gaze point 165 to the gaze point 166.

Figure 12:
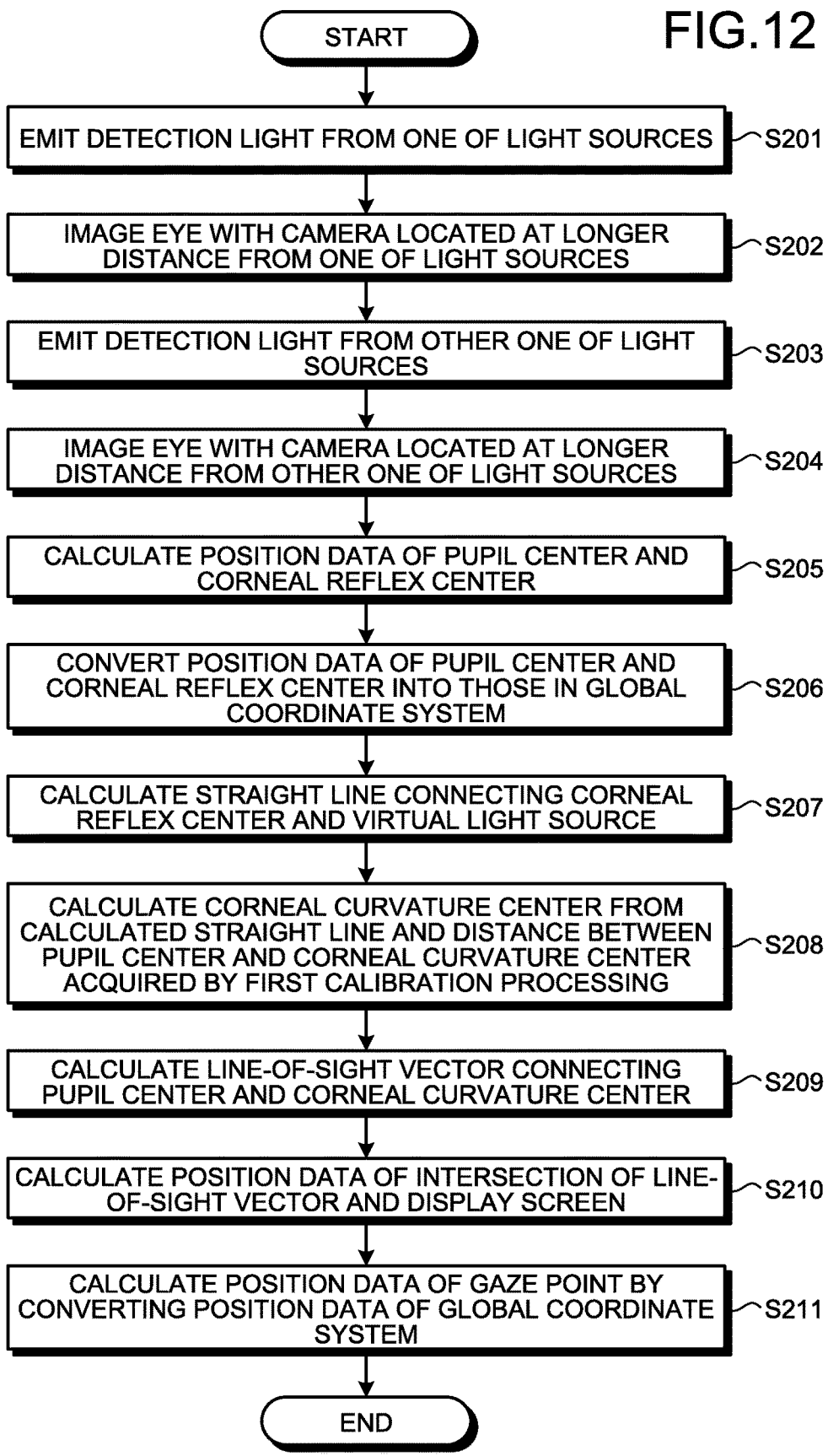
FIG. 12 is a flowchart illustrating an example of the gaze-point detection processing according to the present embodiment.

FIG. 12 is a flowchart illustrating an example of the gaze-point detection processing according to the present embodiment. Note that since processing from step S201 to step S206 illustrated in FIG. 12 is similar to the processing from step S102 to step S107 illustrated in FIG. 10, explanation thereof is omitted. That is, in the gaze point detection processing from step S201 to step S206, position data of the pupil center 112C and the corneal curvature center 110 is calculated by using an image of the eyeball 111 which is captured for the gaze point detection processing and different from the image in the first calibration processing.

After the position data of the pupil center 112C and the corneal reflex center 113C is converted to the global coordinate system at step S206, the gaze point detecting unit 244 calculates a line-of-sight vector connecting the pupil center 112C and the corneal curvature center 110H (step S207). This step S207 is processing same as that at step S113 illustrated in FIG. 10.

Thereafter, the corrected position calculating unit 242 calculates a position that is present on the straight line 173 calculated at step S207, and at which a distance from the pupil center 112C is equal to the distance 126 acquired by the first calibration processing as the corneal curvature center 110H, which is the corrected corneal curvature center (step S208).

The gaze point detecting unit 244 calculates a line-of-sight vector connecting the pupil center 112C and the corneal curvature center 110H (step S209). The line-of-sight vector indicates a direction of sight at which the subject is gazing. The gaze point detecting unit 244 calculates a position of an intersection of the line-of-sight vector and the display screen 101S of the display 101 (step S210). The position of the intersection of the line-of-sight vector and the display screen 101S of the display 101 is a position of a gaze point of the subject on the display screen 101S defined by the three dimensional global coordinate system.

The gaze point detecting unit 244 converts a position of the gaze point defined by the three dimensional global coordinate system to a position on the display screen 101S of the display 101 defined by a two dimensional coordinate system. Thus, the position of the gaze point on the display screen 101S of the display 101 at which the subject gazes is calculated. After the position of the gaze point is converted at step S211, the gaze point detection processing is ended.

Second Calibration Processing

Next, the second calibration processing (step S300) is described. The second calibration processing includes the gaze determination processing, and processing in which a position of an ideal corneal curvature center 110F of each of left and right eyeballs is calculated. The gaze determination processing at the second calibration processing is the same as the gaze determination processing in the first calibration processing, except a point in that image data of the eyeball 111 for the second calibration processing is used.

Figure 13:
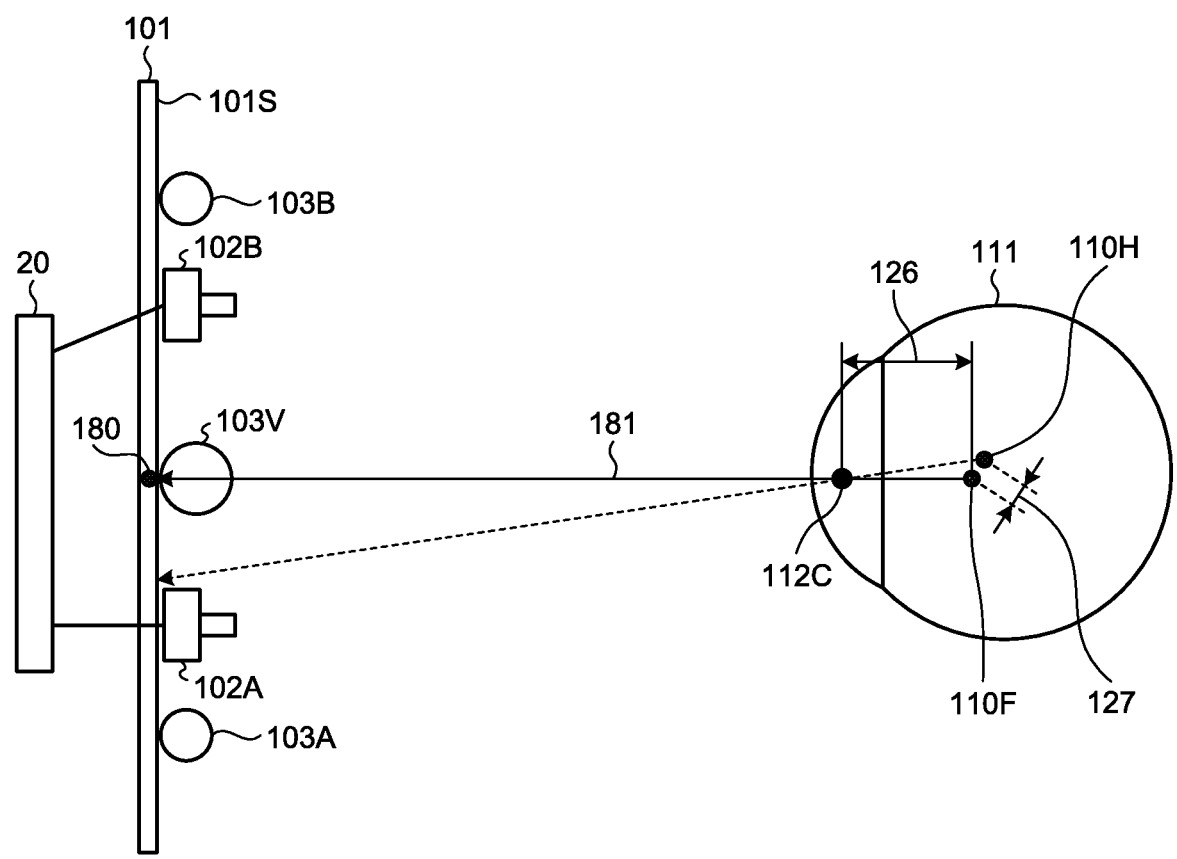
FIG. 13 is a schematic diagram for explaining an example of calibration processing performed by a second calibration unit according to the present embodiment.

FIG. 13 is a schematic diagram for explaining an example of calibration processing performed by the second calibration unit according to the present embodiment. As illustrated in FIG. 13, in the second calibration processing, a target position 180 to be gazed at by the subject is set. The target position 180 is defined in the three dimensional global coordinate system. In the present embodiment, the target position 180 is set, for example, at a center position of the display screen 101S of the display 101. Note that the target position 180 may be set at a position of an end portion of the display screen 101S. The display controller 202 displays a target image at the set target position 180. Thus, the subject is more likely to gaze at the target position 180.

The pupil center 112C indicates a pupil center that is calculated in the first calibration processing. A straight line 181 is a straight line connecting the virtual light source 103V and the pupil center 112C. The distance 126 is a distance between the pupil center 112C and the corneal curvature center 110F that is calculated by the first calibration processing.

At a position that is present on the straight line 181 and has the distance 126 from the pupil center 112C, the ideal corneal curvature center 110F is set. The ideal position calculating unit 252 can calculate a position of the ideal corneal curvature center 110F based on the position of the target position 180, the position of the pupil center 112C, and data of the distance 126 between the pupil center 112C and the corneal curvature center 110. A position difference 127 is a distance between the ideal corneal curvature center 110F and the corrected corneal curvature center 110H described above.

Figure 14:
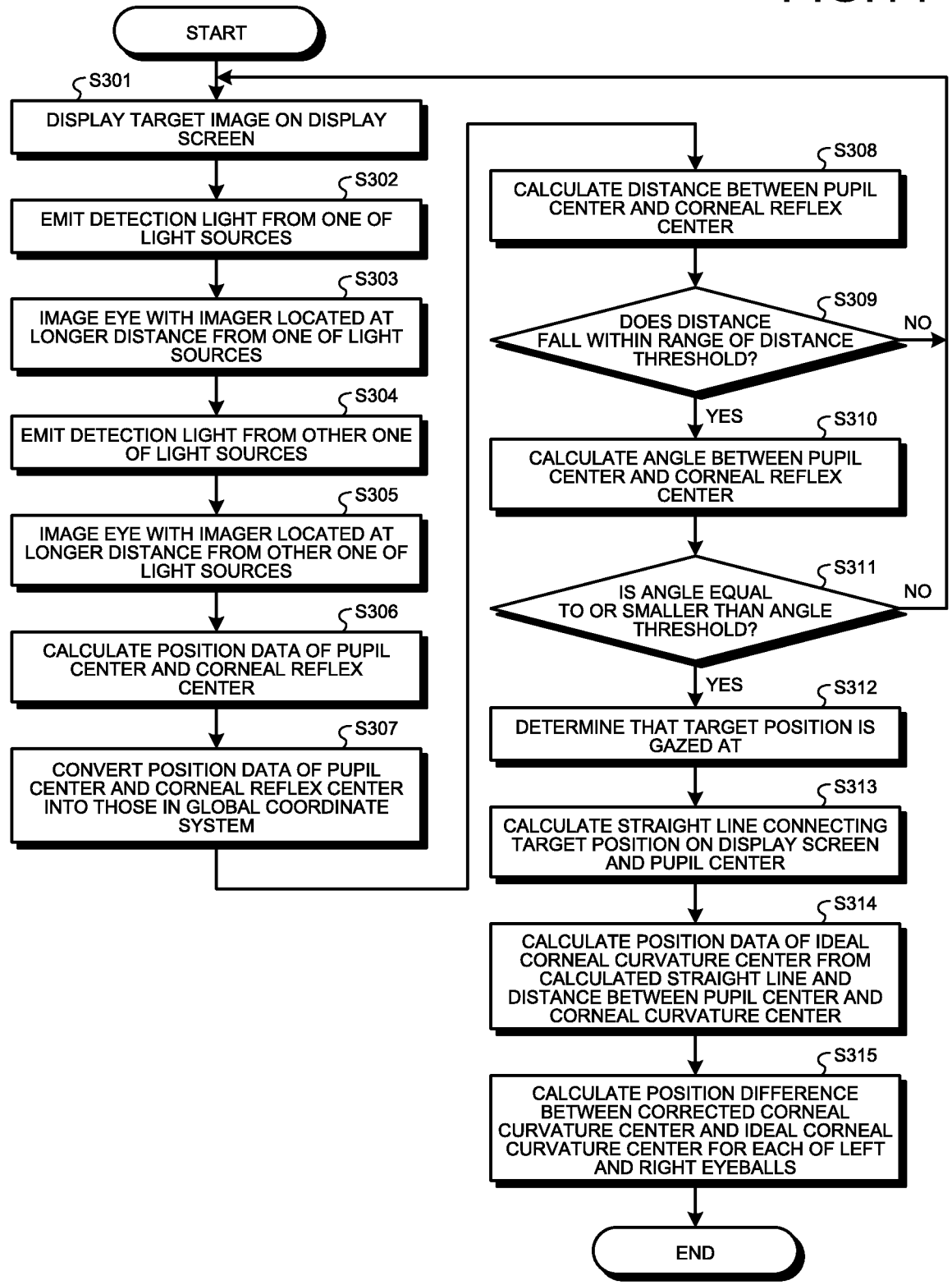
FIG. 14 is a flowchart illustrating an example of second calibration processing according to the present embodiment.

Hereinafter, a flow of the second calibration processing is described based on a processing flow of the second calibration processing. FIG. 14 is a flowchart illustrating an example of the second calibration processing according to the present embodiment. Since the gaze determination processing from step S301 to step S312 illustrated in FIG. 14 is similar to the gaze determination processing from S101 to S112 illustrated in FIG. 10, explanation thereof is omitted. That is, in the gaze determination processing from step S301 to step S312, similarly to the gaze determination processing in the first calibration processing, position data of the pupil center 112C and the corneal reflex center 113C is calculated, and the gaze determining unit 220 determines whether the subject is gazing at the target position 180 based on the position data.

When it is determined that the target position is gazed at step S312, the ideal position calculating unit 252 of the second calibration unit 250 calculates the straight line 181 connecting the target position 180 on the display screen 101S and the pupil center 112C defined by the global coordinate system (step S313).

Next, the ideal position calculating unit 252 acquires a point that is present on the straight line 181 calculated at step S313, and at which a distance from the pupil center 112C is equal to the distance 126 acquired by the first calibration processing as the ideal corneal curvature center 110F, and calculates a position of the ideal corneal curvature center 110F (step S314).

Next, the arithmetic unit 254 calculates the position difference 127 that is a distance between the ideal corneal curvature center 110F and the corrected corneal curvature center 110H for each of the left and right eyeballs (step S315). The arithmetic unit 254 stores the calculated position difference 127 in the storage 212. This position difference 127 is used as a calibration value with respect to the corrected corneal curvature center 110H acquired by the gaze point detection processing. For example, when the gaze point detection processing is performed subsequently, the gaze point detection processing unit 240 detects a line-of-sight direction of each of left and right eyeballs from the position of the pupil center 112C and a position in which the position difference 127 is added to the position of the corrected corneal curvature center 110H. Specifically, the gaze point-detection processing unit 240 detects a line-of-sight vector traveling toward the pupil center 112C from the corneal curvature center obtained by adding the position difference 127 as the calibration value to the corrected corneal curvature center 110H as the line-of-sight of the subject after calibration. At this step S315, the second calibration processing is ended.

As described above, the eye tracking device 100 according to the present embodiment includes the light source (the first light source 103A and the second light source 103B in the present embodiment), the imager (the first camera 102A and the second camera 102B in the present embodiment), the position detecting unit 210, the gaze determining unit 220, and the calibration unit (the first calibration unit 230 and the second calibration unit 250 in the present embodiment). The light source irradiates the detection light for eye tracking to the eyeball 111 of a subject. The imager images the eyeball 111 of the subject to which the detection light is irradiated. The position detecting unit 210 detects a position of the pupil center 112C of the eyeball 111, and a position of the corneal reflex center 113C of the eyeball 111. The gaze determining unit 220 determines whether the subject is gazing at a target position based on the position of the pupil center 112C and the position of the corneal reflex center 113C detected by the position detecting unit 210. The calibration unit performs calibration (the first calibration and the second calibration in the present embodiment) for eye tracking based on the image captured by the imager when the gaze determining unit 220 determines that the target position is gazed at.

The calibration at the eye tracking is performed assuming that the subject is gazing at a target position on the display screen 101S. Accordingly, if calibration is performed when the subject is not gazing at the target position, the accuracy of calibration can be deteriorated. On the other hand, the eye tracking device 100 according to the present embodiment determines whether the subject is gazing at the target position, and performs the calibration processing when it is determined that the target position is gazed at. Therefore, the eye tracking device 100 according to the present embodiment avoids calibration from being performed in a state in which a subject is not gazing at a target position, and can suppress deterioration of accuracy of calibration. Moreover, the eye tracking device 100 according to the present embodiment determines whether a subject is gazing at a target position based on a position of the pupil center 112C and a position of the corneal reflex center 113C and, therefore, is possible to determine whether the subject is gazing at the target position highly accurately, and to suppress deterioration of accuracy of calibration appropriately.

Furthermore, the gaze determining unit 220 determines that a subject is gazing at a target position when an index value indicating a relationship between the position of the pupil center 112C and a position of the corneal reflex center 113C falls within a range of a predetermined threshold. Furthermore, the gaze determining unit 220 determines that the subject tis not gazing at the target position when the index value falls outside the range of the threshold. The eye tracking device 100 determines whether the subject is gazing at the target position based on whether the index value indicating the relationship between a position of the pupil center 112C and a position of the corneal reflex center 113C falls within the range of the threshold. Therefore, the eye tracking device 100 can determine whether a subject is gazing at a target position highly accurately, and can suppress deterioration of accuracy of calibration appropriately.

Moreover, the gaze determining unit 220 determines that a subject is gazing at a target position when the distance r between a position of the pupil center 112C and a position of the corneal reflex center 113C falls within a range of the predetermined distance threshold r0. The eye tracking device 100 makes determination based on whether the distance r falls within the range of the distance threshold r0 and, therefore, can determine whether a subject is gazing at a target position highly accurately, and can suppress deterioration of accuracy of calibration appropriately.

Furthermore, the gaze determining unit 220 determines that a subject is gazing at a target position when the angle θ between a straight line connecting a position of the pupil center 112C and the predetermined reference point P and a straight line connecting the position of the pupil center 112C and a position of the corneal reflex center 113C is equal to or smaller than the predetermined angle threshold θ0. The eye tracking device 100 makes determination based on whether the angle θ is equal to or smaller than the angle threshold θ0 and, therefore, can determine whether a subject is gazing at a target position highly accurately, and can suppress deterioration of accuracy of calibration appropriately.

Second Embodiment

Next, a second embodiment is described. The eye tracking device 100 according to the second embodiment differs from the first embodiment in a point in which a threshold for determination is gradually updated. In the second embodiment, description about configurations common with the first embodiment is omitted.

The gaze determining unit 220 according to the second embodiment determines that a subject is gazing at a target position when an index value indicating a relationship between a position of the pupil center 112C and a position of the corneal reflex center 113C falls within a range of a predetermined threshold, similarly to the first embodiment. Moreover, the gaze determining unit 220 according to the second embodiment determines that the subject is not gazing at the target position when the index value falls outside the range of the threshold. The gaze determining unit 220 according to the second embodiment changes, unlike the first embodiment, a value of the threshold after determining whether the subject is gazing at the target position, and determines whether the index value falls within a range of the changed threshold. The gaze determining unit 220 according to the second embodiment determines whether the index value falls within the range of the changed threshold to determine whether the subject is gazing at the target position again.

In more detail, the gaze determining unit 220 updates the threshold such that a numeric range is widened when it is determined that the index value falls outside the range of the threshold and the subject is not gazing at the target position to ease a determination criteria. The eye tracking device 100 according to the second embodiment again acquires an image of the eyeball 111, and again detects a position of the pupil center 112C and a position of the corneal reflex center 113C based on the image. The eye tracking device 100 then calculates an index value indicating the relationship between the position of the pupil center 112C and the position of the corneal reflex center 113C again, and determines whether the index value falls within the range of the updated threshold (threshold having a wider range) again. The gaze determining unit 220 determines that the subject is gazing at the target position when the index value falls within the range of the updated threshold.

For example, when the threshold is kept constant, a state in which the index value falls outside the range of the threshold maintains even if the determination is performed again with the newly captured image, and it can take time to finish the calibration. However, in the second embodiment, the determination is performed again in a state in which the threshold is updated to ease the determination criteria when the index value has not fallen in a range of the threshold once. Therefore, in the second embodiment, it is possible to suppress deterioration of a success rate of calibration, and to suppress increase of time until the calibration is finished.

The gaze determining unit 220 may further update the threshold such that the numeric range is more widened when the recalculated index value falls outside the updated threshold to further ease the determination criteria. The gaze determining unit 220 may re-determine whether the subject is gazing at the target position in a state in which the determination criteria is eased. Note that it is preferable that an upper limit be set for the update of the threshold. For example, the gaze determining unit 220 may have three levels to the threshold with setting the upper limit for the number of change of the threshold to two. Moreover, the gaze determining unit 220 may set an upper limit for elapsed time from when the threshold is set, and may stop further update of the threshold when the elapsed time reaches the upper limit. Thus, it is possible to suppress deterioration of accuracy of calibration with the determination criteria being eased too much.

Note that the index value in the present embodiment is the distance r and the angle $\theta$. The gaze determining unit 220 updates the distance threshold r0 to an updated distance threshold r1 when it is determined that the distance r falls outside the range of the distance threshold r0. The updated distance threshold r1 has a numeric range set to be wider than the numeric range of the distance threshold r0. The updated distance range r1 is preferable to have a numeric range expanded by 20% to 30% from the distance threshold r0. Furthermore, the gaze determining unit 220 may further update the updated distance threshold r1 to an updated distance threshold r2 when it is determined that the distance r falls outside the range of the updated distance threshold r1, and may determine whether the re-calculated distance r falls within a range of the updated distance threshold r2. An expansion rate of the numeric range of the updated distance threshold r2 with respect to the updated distance threshold r1 is, for example, same as the expansion rate of the numeric range of the updated distance threshold r1 with respect to the distance threshold r0.

Moreover, the gaze determining unit 220 updates the angle threshold $\theta 0$ to an updated angle threshold $\theta 1$ when it is determined that the angle $\theta$ is larger than the angle threshold $\theta 0$ (or falls outside the range of the angle threshold $\theta$). The updated angle threshold $\theta 1$ is a larger numeric value (or a numeric range set to have a wider numeric range) than the angle threshold $\theta 0$. The updated angle threshold $\theta 1$ is preferable to be a larger value (or a numeric range expanded) by 20% to 30% from the angle threshold $\theta 0$. Furthermore, the gaze determining unit 220 may further update the updated angle threshold $\theta 1$ to an updated angle threshold $\theta 2$ when it is determined that the recalculated angle $\theta$ is larger than the update angle threshold $\theta 1$ (or out of a range of the updated angle threshold $\theta 1$), and may determine whether the re-calculated angle $\theta$ is smaller than the update threshold $\theta 2$ (or falls within a range of the update angle threshold $\theta 2$). An expansion rate of the updated angle threshold $\theta 2$ with respect to the updated angle threshold $\theta 1$ is, for example, same as the expansion rate of the updated angle threshold $\theta 1$ with respect to the angle threshold $\theta 0$. Moreover, it is preferable that the expansion rate of the updated angle threshold $\theta 1$ with respect to the angle threshold $\theta 0$ be smaller than the expansion rate of the updated distance threshold r1 with respect to the distance threshold r0. The angle $\theta$ can be more important than the distance r in determination whether the target position is gazed at. Therefore, by making the expansion rate of the angle threshold $\theta 0$ smaller than the expansion rate of the distance threshold r0, it is possible to avoid the determination criteria from being eased too much, and to suppress deterioration of accuracy of calibration.

As described, in the present embodiment, when it is determined that an index value falls outside a range of a threshold and a subject is not gazing at a target position, the threshold is updated to have a wider numeric range to ease the determination criteria. However, as long as the gaze determining unit 220 determines again whether the target position is gazed at by determining whether the index value falls within a range of the threshold, it is not limited to easing the determination criteria. For example, the gaze determining unit 220 may update the threshold to narrow a numeric range to make the determination criteria stricter when it is determined that the index value falls within the range of the threshold and that the subject is gazing at the target position. The gaze determining unit 220 may then again determine whether the index value falls within a range of an updated threshold (threshold having a narrower numeric range). The gaze determining unit 220 updates the threshold such that the numeric range is narrowed and repeats determination when it is determined that the index value falls within a range of the updated threshold (threshold having narrower numeric range). When it is determined that the index value falls outside the updated threshold (range having a narrowed numeric range), the gaze determining unit 220 regards data used for the last determination just before the current determination as data for the calibration. Thus, the gaze determining unit 220 can further improve the accuracy of the calibration.

Figure 15:
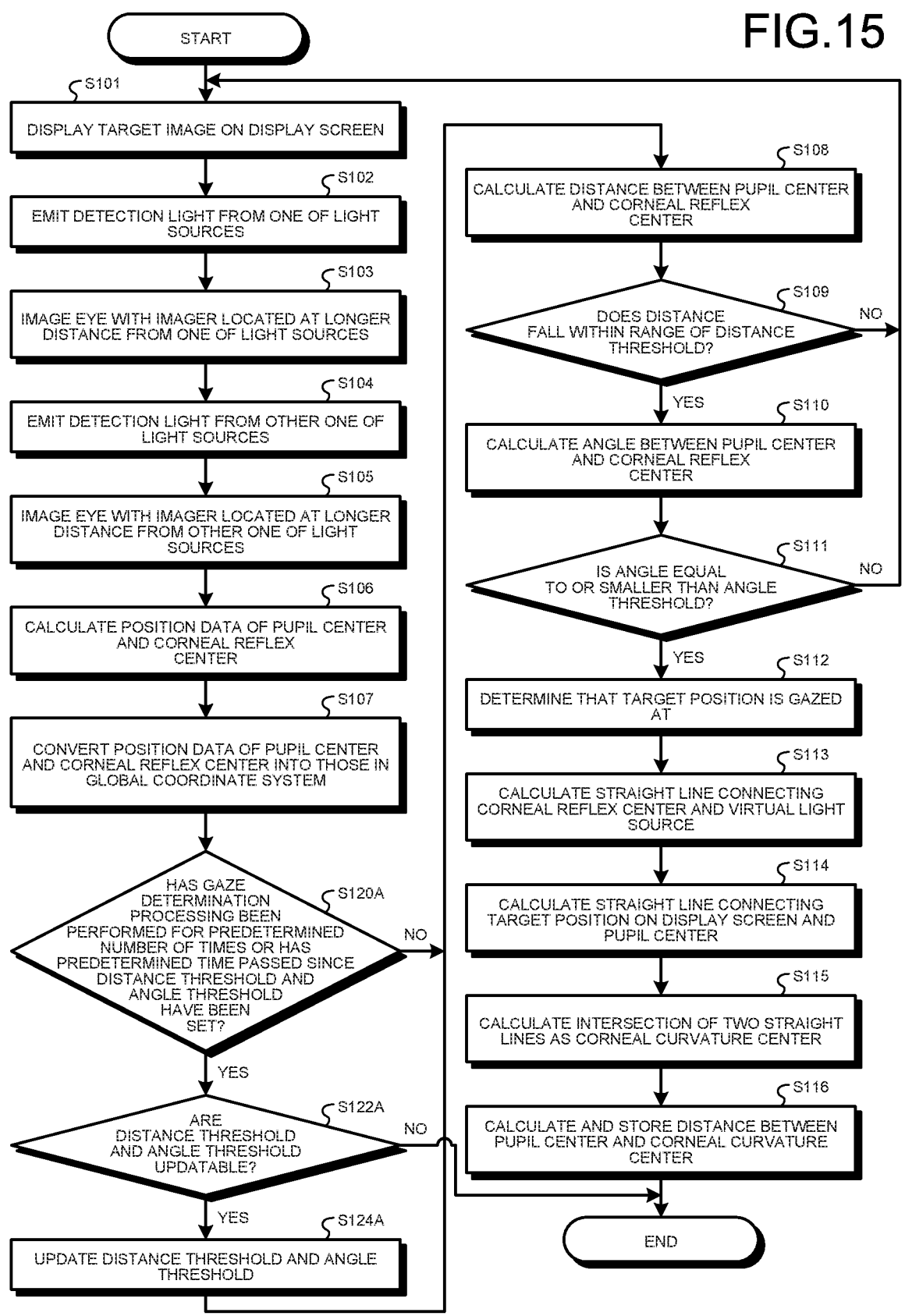
FIG. 15 is a flowchart for explaining an example of first calibration processing according to a second embodiment.

The processing according to the second embodiment described above is described with a flowchart. First, first calibration processing according to the second embodiment is described. FIG. 15 is a flowchart for explaining an example of the first calibration processing according to the second embodiment. As illustrated in FIG. 15, the eye tracking device 100 according to the second embodiment performs step S101 to step S107 similarly to the first embodiment (refer to FIG. 10), to calculate the positions of the pupil center 112C and the corneal reflex center 113C.

Next, the gaze determining unit 220 determines whether the gaze determination processing has been performed for a predetermined number of times since the distance threshold r0 and the angle threshold θ0 are set, or whether a predetermined time has passed since the distance threshold r0 and the angle threshold θ0 are set (step S120A). The predetermined number of times is, for example, one, and the predetermined time is time required to perform the gaze determination processing once. That is, the gaze determining unit 220 determines whether the gaze determination processing has been performed previously.

When it is determined that the gaze determination processing has not been performed for the predetermined number of times, or that the predetermined time has not passed (step S120A: NO), it proceeds to step S108, and the gaze determination processing is performed by using the distance threshold r0 and the angle threshold θ0 before update. That is, in this case, the gaze determining unit 220 determines that the gaze determination processing has not been performed, and performs the first gaze determination processing. Processing after step S108 is similar to that in the first embodiment. However, in the second embodiment, it may return to step S120A instead of returning to step S101 when it is determined that the distance r falls outside the range of the distance threshold r0 (or an updated distance threshold) at step S109 (step S109: NO), and when it is determined that the angle θ is not smaller than the angle threshold 0 (or an updated angle threshold) at step S111 (step S111: NO). In this case, it is possible to perform re-determination with an updated threshold for the same data, and to further reduce time used for the calibration.

On the other hand, when it is determined that the gaze determination processing has been performed for the predetermined number of times, or that the predetermined time has passed (step S120A: YES), the gaze determining unit 220 determines whether the distance threshold r0 and the angle threshold θ0 are updatable (step S122A). As described above, an upper limit for update of the distance threshold r0 and the angle threshold θ0 is predetermined. The gaze determining unit 220 determines that the distance threshold r0 and the angle threshold θ0 are updatable when the distance threshold r0 and the angle threshold θ0 have not been updated up to the upper limit, and determines not updatable when they have been updated to the upper limit.

When it is determined that the distance threshold r0 and the angle threshold θ0 are not updatable (step S122A: NO), the gaze determining unit 220 judges that it is an error, and the processing is ended. In this case, for example, an error message indicating that calibration cannot be performed appropriately, or the like may be provided to the operator or the subject.

On the other hand, when it is determined that the distance threshold r0 and the angle threshold θ0 are updatable (step S122A: YES), the gaze determining unit 220 updates the distance threshold r0 and the angle threshold θ0 (step S124A), and it proceeds to step S108 to perform the gaze determination processing again with the updated distance threshold r0 and angle threshold θ0. At completion of step S116, the processing is ended.

Figure 16:
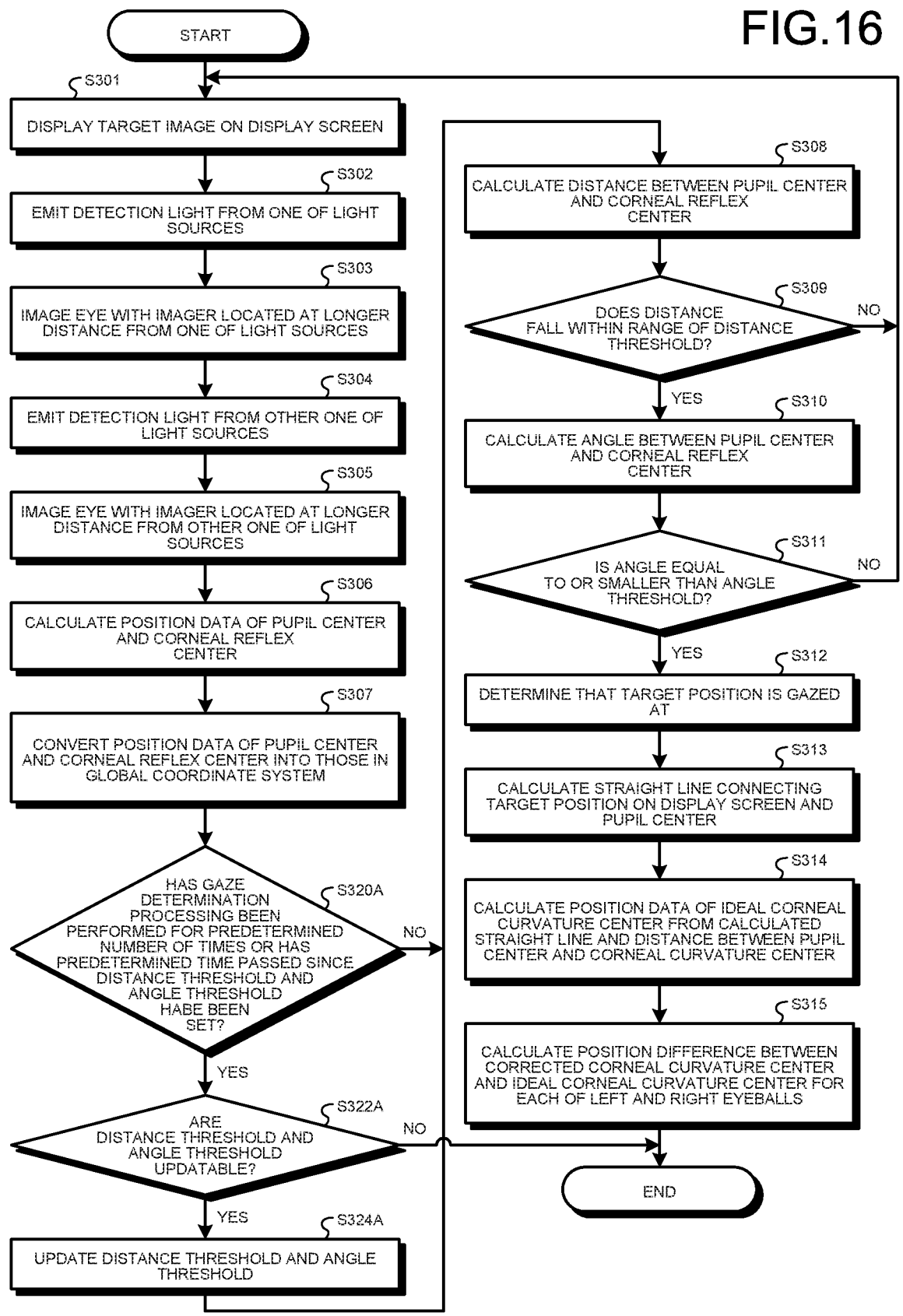
FIG. 16 is a flowchart for explaining an example of second calibration processing according to the second embodiment.

Next, second calibration processing according to the second embodiment is described. FIG. 16 is a flowchart for explaining an example of the second calibration processing according to the second embodiment. As illustrated in FIG. 16, the eye tracking device 100 according to the second embodiment performs step S301 to step S307 similarly to the first embodiment (refer to FIG. 14) to calculate positions of the pupil center 112C and the corneal reflex center 113C.

Next, the gaze determining unit 220 determines whether the gaze determination processing has been performed for the predetermined number of times since the distance threshold r0 and the angle threshold θ0 are set, or whether predetermined time has passed since the distance threshold r0 and the angle threshold θ0 are set (step S320A). The gaze determining unit 220 determines whether the gaze determination processing has been performed previously.

When it is determined that the gaze determination processing has not been performed for the predetermined number of times, or that the predetermined time has not been passed (step S320A: NO), it proceeds to step S308, and the gaze determination processing is performed by using the distance threshold r0 and the angle threshold θ0 before update. That is, in this case, the gaze determining unit 220 determines that the gaze determination processing has not been performed, and performs the first gaze determination processing. Processing after step S308 is similar to that in the first embodiment. However, in the second embodiment, it may return to step S320A instead of returning to step S301 when it is determined that the distance r falls outside the range of the distance threshold r0 (or an updated distance threshold) at step S309 (step S309: NO), and when it is determined that the angle θ is not smaller than the angle threshold θ0 (or an updated angle threshold) at step S311 (step S311: NO). In this case, it is possible to perform re-determination with an updated threshold for the same data, and to further reduce time used for the calibration.

On the other hand, when it is determined that the gaze determination processing has been performed for the predetermined number of times, or that the predetermined time has passed (step S320A: YES), the gaze determining unit 220 determines whether the distance threshold r0 and the angle threshold θ0 are updatable (step S322A). The gaze determining unit 220 determines that the distance threshold r0 and the angle threshold θ0 are updatable when the distance threshold r0 and the angle threshold θ0 have not been updated up to the upper limit, and determines not updatable when they have been updated to the upper limit.

When it is determined that the distance threshold r0 and the angle threshold θ0 are not updatable (step S322A: NO), the gaze determining unit 220 judges that it is an error, and ends the processing.

On the other hand, when it is determined that the distance threshold r0 and the angle threshold θ0 are updatable (step S322A: YES), the gaze determining unit 220 updates the distance threshold r0 and the angle threshold θ0 (step S324A), and performs the gaze determination processing by using the updated distance threshold r0 and angle threshold θ0 with proceeding to step S308. At completion of step S315, the processing is ended. As described, the processing from step S320A to step S324A is similar to that at step S120A to step S124A illustrated in FIG. 15.

As described above, the gaze determining unit 220 according to the second embodiment changes a threshold after determining whether a subject is gazing at a target position, and determines whether an index value falls within a range of a changed threshold, thereby re-determining whether the subject is gazing at the target position. The eye tracking device 100 according to the second embodiment can thereby suppress deterioration of a success rate of calibration, and suppress deterioration of accuracy of calibration more preferably.

As above, the embodiments of the present application have been described, but embodiments are not limited to these embodiments. Moreover, the components described above include those that can be easily thought of by those skilled in the art, substantially the same elements, and those in a range of so-called equivalents. Furthermore, the components described above can be appropriately combined. Moreover, various kinds of omission, replacement, and change are possible within a range not departing from a scope of the gist of the embodiments described above.

According to the present application, deterioration of accuracy of calibration can be suppressed.

Although the application has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An eye tracking device comprising:
at least one light source configured to irradiate detection light for eye tracking to at least one eyeball of a subject;
at least one imager configured to capture an image of the at least one eyeball;
a memory that is configured to store computer-executable instructions; and
a processor that is configured to execute the computer-executable instructions to perform operations, the operations comprising:
detecting a position of a pupil center of the at least one eyeball and a position of a corneal reflex center of the at least one eyeball from the image captured by the at least one imager;
in response to determining that a distance between the position of the pupil center and the position of the corneal reflex center falls outside a range of the predetermined distance threshold, determining that the subject is not gazing at a target position; and
in response to determining that the distance between the position of the pupil center and the position of the corneal reflex center falls within the range of the predetermined distance threshold, determining that the subject is gazing at the target position and initiating calibration for the eye tracking based on the image, wherein the calibration comprises calculating a line-of-sight vector connecting the pupil center and a corneal curvature center of the at least one eyeball.

2. The eye tracking device according to claim 1, wherein the determining that the subject is gazing at the target position is further based on a determination that an angle between a straight line connecting the position of the pupil center and a predetermined reference point and a straight line connecting the position of the pupil center and the position of the corneal reflex center is equal to or smaller than a predetermined angle threshold, and
the determining that the subject is not gazing at the target position is further based on a determination that the angle between the straight line connecting the position of the pupil center and the predetermined reference point and the straight line connecting the position of the pupil center and the position of the corneal reflex center is larger than the predetermined angle threshold.

3. The eye tracking device according to claim 2, wherein the operations further comprise changing the predetermined distance threshold or the predetermined angle threshold after determining whether the subject is gazing at the target position, and re-determining whether the subject is gazing at the target position.

4. An eye tracking method comprising:
irradiating detection light for eye tracking to at least one eyeball of a subject;
capturing an image of the at least one eyeball;
detecting a position of a pupil center of the at least one eyeball and a position of a corneal reflex center of the at least one eyeball from the image;
in response to determining that a distance between the position of the pupil center and the position of the corneal reflex center falls outside a range of a predetermined distance threshold, determining that the subject is not gazing at a target position, and
in response to determining that the distance between the position of the pupil center and the position of the corneal reflex center falls within the range of the predetermined distance threshold:
determining that the subject is gazing at the target position, and
initiating a calibration sequence for the eye tracking based on the image of the at least one eyeball, wherein the calibration sequence comprises at least calculating a line-of-sight vector connecting the pupil center and a corneal curvature center of the at least one eyeball.

* * * * *